United States Patent
Delvalle et al.

(10) Patent No.: US 9,192,564 B2
(45) Date of Patent: Nov. 24, 2015

(54) SACCHARIDE SILOXANE COPOLYMERS AND METHODS FOR THEIR PREPARATION AND USE

(75) Inventors: Cindy Delvalle, Uccle (BE); Eric Jude Joffre, Midland, MI (US); Concettina Scavuzzo, Chap.-Lez-Herlaimont (BE); Simon Toth, Midland, MI (US); Isabelle Van Reeth, Shanghai (CN)

(73) Assignee: Dow Corning Corporation, Midland, MI (US)

( * ) Notice: Subject to any disclaimer, the term of this patent is extended or adjusted under 35 U.S.C. 154(b) by 101 days.

(21) Appl. No.: 13/817,634

(22) PCT Filed: Aug. 15, 2011

(86) PCT No.: PCT/US2011/047715
§ 371 (c)(1), (2), (4) Date: Feb. 19, 2013

(87) PCT Pub. No.: WO2012/027143
PCT Pub. Date: Mar. 1, 2012

(65) Prior Publication Data
US 2013/0149259 A1    Jun. 13, 2013

Related U.S. Application Data

(60) Provisional application No. 61/375,938, filed on Aug. 23, 2010, provisional application No. 61/407,980, filed on Oct. 29, 2010.

(51) Int. Cl.
*A61K 8/898* (2006.01)
*A61K 8/06* (2006.01)
*A61Q 19/00* (2006.01)
*C08G 77/388* (2006.01)
*C08G 77/42* (2006.01)

(52) U.S. Cl.
CPC . *A61K 8/898* (2013.01); *A61K 8/06* (2013.01); *A61K 8/064* (2013.01); *A61Q 19/00* (2013.01); *C08G 77/388* (2013.01); *C08G 77/42* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 5,004,791 A | 4/1991 | Billmers | |
| 5,891,977 A | 4/1999 | Dietz et al. | |
| 6,066,727 A | 5/2000 | Yamamoto et al. | |
| 6,255,429 B1 | 7/2001 | Griffin et al. | |
| 6,471,952 B1 | 10/2002 | Dubief et al. | |
| 6,762,289 B1 | 7/2004 | O'Lenick, Jr. et al. | |
| 8,304,568 B2 | 11/2012 | Herzig | |
| 2008/0138386 A1 | 6/2008 | Joffre et al. | |
| 2008/0197315 A1 | 8/2008 | Schmidt et al. | |
| 2008/0199417 A1* | 8/2008 | Joffre et al. | 424/70.12 |
| 2008/0200612 A1 | 8/2008 | Joffre et al. | |
| 2008/0209645 A1 | 9/2008 | Carrillo et al. | |
| 2009/0258058 A1 | 10/2009 | Thomas et al. | |
| 2013/0102686 A1 | 4/2013 | Tamura et al. | |
| 2013/0115184 A1 | 5/2013 | Beck et al. | |
| 2013/0149261 A1 | 6/2013 | Delvalle et al. | |

FOREIGN PATENT DOCUMENTS

| | | | |
|---|---|---|---|
| JP | 62068820 | 3/1987 | |
| JP | 2008-546919 | 12/2008 | |
| JP | 2011-102362 | 5/2011 | |
| WO | 9429324 | 12/1994 | |
| WO | 0288456 | 11/2002 | |
| WO | 2006127924 | 11/2006 | |
| WO | WO 2006/127924 * | 11/2006 | C08G 77/42 |
| WO | 2008103219 | 8/2008 | |
| WO | WO 2009/019144 | 2/2009 | |
| WO | 2009125126 | 10/2009 | |

* cited by examiner

*Primary Examiner* — Brian Gulledge
(74) *Attorney, Agent, or Firm* — Nixon Peabody LLP

(57) ABSTRACT

A novel saccharide siloxane copolymer is useful in personal care compositions. The saccharide siloxane copolymer may be used as a universal emulsifier to prepare low odor emulsions for personal care applications.

38 Claims, No Drawings

SACCHARIDE SILOXANE COPOLYMERS AND METHODS FOR THEIR PREPARATION AND USE

CROSS REFERENCE TO RELATED APPLICATIONS

This application is a U.S. national stage filing under 35 U.S.C. §371 of PCT Application No. PCT/US11/47715 filed on Aug. 15, 2011, currently pending, which claims the benefit of U.S. Provisional Patent Application No. 61/375,938 filed Aug. 23, 2010 and U.S. Provisional Patent Application No. 61/407,980 filed Oct. 29, 2010 under 35 U.S.C. §119 (e). PCT Application No. PCT/US11/47715 and U.S. Provisional Patent Application No. 61/375,938 and U.S. Provisional Patent Application No. 61/407,980 are hereby incorporated by reference.

BACKGROUND OF THE INVENTION

Saccharide siloxanes are known in the art. Saccharide siloxanes comprising a hydroxyl functional saccharide component and an organosiloxane component were found to be useful when applied to hair, skin, fabric, paper, wood and other substrates. The saccharide component may be covalently bound to the organosiloxane at one or more pendant or terminal positions, or some combination thereof, through linkages including but not limited to ether, ester, and amide bonds.

BRIEF SUMMARY OF THE INVENTION

A saccharide siloxane copolymer (copolymer) has formula:

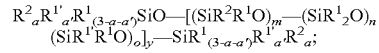

where
each $R^1$ can be the same or different and each $R^1$ comprises hydrogen, an alkyl group of 1 to 12 carbon atoms, an organic group, or a group of formula $R^3$-Q;
  Q comprises an epoxy, cycloalkylepoxy, primary or secondary amino, ethylenediamine, carboxy, halogen, vinyl, allyl, anhydride, or mercapto functionality;
each $R^{1'}$ is a long chain organic group;
subscript m has an average value ranging from 0 to 10,000;
subscript n has an average value ranging from 0 to 10,000 and may be the same or different;
subscript o has an average value ranging from 0 to 10,000;
each subscript a is independently 0, 1, 2, or 3;
each subscript a' is independently 0, 1, 2, or 3;
subscript y is an integer such that the copolymer has a molecular weight less than 1 million;
each $R^2$ has formula $Z$-$(G^1)_b$-$(G^2)_c$, and there is an average of at least one $R^2$ per copolymer molecule, where
  $G^1$ is a saccharide component comprising 5 to 12 carbon atoms,
  a quantity (b+c) has a value ranging from 1 to 10, and subscript b or subscript c can be 0,
  $G^2$ is a saccharide component comprising 5 to 12 carbon atoms additionally substituted with organic or organosilicon radicals,
  each Z is a linking group and is independently selected from the group consisting of:
    —$R^3$—NHC(O)—$R^4$—;
    —$R^3$—NHC(O)O—$R^4$—;
    —$R^3$—NH—C(O)—NH—$R^4$—;
    —$R^3$—C(O)—O—$R^4$—;
    —$R^3$—O—$R^4$—;
    —$R^3$—CH(OH)—$CH_2$—O—$R^4$—;
    —$R^3$—S—$R^4$—;
    —$R^3$—CH(OH)—$CH_2$—NH—$R^4$—;
    —$R^3$—N($R^1$)—$R^4$—;
    —NHC(O)—$R^4$—;
    —NHC(O)O—$R^4$—;
    —NH—C(O)—NH—$R^4$—;
    —C(O)—O—$R^4$—;
    —O—$R^4$—;
    —CH(OH)—$CH_2$—O—$R^4$—;
    —S—$R^4$—;
    —CH(OH)—$CH_2$—NH—$R^4$—;
    —N($R^1$)—$R^4$—;
    —$R^3$—NHC(O)—;
    —$R^3$—NHC(O)O—;
    —$R^3$—NH—C(O)—NH—;
    —$R^3$—C(O)—O—;
    —$R^3$—O—;
    —$R^3$—CH(OH)—$CH_2$—O—;
    —$R^3$—S—;
    —$R^3$—CH(OH)—$CH_2$—NH—;
    —$R^3$—N($R^1$)—;
    —$R^3$—N($R^8$)—C(O)—$R^4$—,
    —$R^3$—CH(OH)—$CH_2$—N($R^8$)—$R^4$—, or
    —$R^3$—CH(N($R^4$)($R^8$))$CH_2OH$;
  where each $R^3$ and each $R^4$ are divalent spacer groups comprising a group of formula $(R^5)_r(R^6)_s(R^7)_t$, where at least one of subscripts r, s and t is 1, and each $R^5$ and each $R^7$ are independently an alkylene group of 1 to 12 carbon atoms,
  each $R^6$ is —N($R^8$)—, where $R^8$ is selected from $R^3$, a group of formula Z—X, a monovalent hydrocarbon group, or a reaction product of —N(H)— with an epoxy functional group, a cycloalkylepoxy functional group, a glycidyl ether functional group, an acidic anhydride functional group, or a lactone;
  each X is independently a divalent carboxylic acid, phosphate, sulfate, sulfonate or quaternary ammonium radical, and
with the provisos that
  at least one of $R^3$ and $R^4$ must be present in the linking group, and
  each $R^3$ and each $R^4$ may be the same or different.

DETAILED DESCRIPTION OF THE INVENTION

A saccharide siloxane copolymer (copolymer) comprises a saccharide component and a siloxane component. The siloxane component forms the backbone of the copolymer molecule. Saccharide components may be bonded to the siloxane backbone in terminal groups, pendant groups, or both terminal and pendant groups. Alternatively, the saccharide component may be bonded to the siloxane backbone in a pendant group.

The copolymer may be a solid or a fluid under ambient conditions of temperature and pressure, e.g., at 25° C. and 760 mmHg. Whether the copolymer is a solid at ambient conditions, or a fluid such as a liquid or a gum, depends on various factors including the degree of polymerization (DP) of the copolymer. The copolymer may have a DP ranging from 2 to 15,000, alternatively 5 to 10,000, alternatively 50 to 5,000, alternatively 100 to 1,000, alternatively 50 to 1,000, alternatively 50 to 500, and alternatively 100 to 400. The copolymer may be useful in personal care compositions.

Alternatively, the copolymer may be useful as an emulsifier. The copolymer may be useful as a universal emulsifier, e.g., for water in oil (w/o) type emulsions, such as water in silicone emulsions or water in organic oil type emulsions. The copolymer useful as a universal emulsifier may be a fluid under ambient conditions of temperature and pressure. The viscosity of the fluid copolymer depends on various factors including the DP of the copolymer. The copolymer useful as a universal emulsifier may have a DP ranging from 2 to 500, alternatively 5 to 500, alternatively, 25 to 500, alternatively 50 to 450, alternatively 100 to 400, and alternatively 50 to 350.

The copolymer has formula:

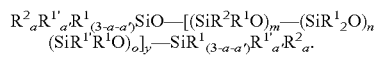

$R^2{}_a R^{1'}{}_{a'} R^1{}_{(3-a-a')}SiO-[(SiR^2R^1O)_m-(SiR^1{}_2O)_n(SiR^{1'}R^1O)_o]_y-SiR^1{}_{(3-a-a')}R^{1'}{}_{a'}R^2{}_a$.

In this formula, each $R^1$ can be the same or different. Each $R^1$ comprises hydrogen, an alkyl group of 1 to 12 carbon atoms, an organic group, or a group of formula $R^3$-Q. Group Q comprises an epoxy, cycloalkylepoxy, primary or secondary amino, ethylenediamine, carboxy, halogen, vinyl, allyl, anhydride, or mercapto functionality. Each $R^{1'}$ is a monovalent organic group having at least 13 member atoms. $R^{1'}$ may be a hydrocarbon group, such as an alkyl, alkenyl, alkynyl, aryl, alkaryl, cycloalkyl, or cycloalkenyl; or an ester functional group. Each $R^{1'}$ may be unbranched or branched. Each $R^{1'}$ may be saturated or partially unsaturated. $R^{1'}$ is exemplified by an alkyl group with an average of at least 14 carbon atoms. Such alkyl groups for $R^{1'}$ are exemplified by alkyl groups of 13 to 40 carbon atoms, such as $-C_{13}H_{27}$, $-C_{14}H_{29}$, $-C_{15}H_{31}$, $-C_{16}H_{33}$, $-C_{17}H_{35}$, $-C_{18}H_{37}$, $-C_{19}H_{39}$, $-C_{20}H_{41}$, $-C_{21}H_{43}$, $-C_{22}H_{45}$, $-C_{23}H_{47}$, $-C_{24}H_{49}$, $-C_{25}H_{51}$, $-C_{26}H_{53}$, $-C_{27}H_{55}$, $-C_{28}H_{57}$, $-C_{29}H_{59}$, $-C_{30}H_{61}$, $-C_{31}H_{63}$, $-C_{32}H_{65}$, $-C_{33}H_{67}$, $-C_{34}H_{69}$, $-C_{35}H_{71}$, $-C_{36}H_{73}$, $-C_{37}H_{75}$, $-C_{38}H_{77}$, $-C_{39}H_{79}$, $-C_{40}H_{81}$, and combinations thereof.

Subscripts m and n each have average values ranging from 0 to 15,000; alternatively 0 to 10,000; and alternatively 0 to 500, and may be the same or different. Subscript o has an average value ranging from 0 to 10,000; alternatively 0 to 2,500; alternatively 1 to 20; and alternatively 1 to 10. Alternatively, subscript m may be greater than 0 to 1, subscript n may be 40 to 65, and subscript o may be 5 to 25. Alternatively, the ratio of subscript m/(m+n+o) may be up to 0.05 for some applications, such as when the copolymer will be used as an emulsifier in certain emulsions. Alternatively, the ratio of subscript m/(m+n+o) may be 0.001 to 0.05. The ratio of subscript n/(m+n+o) may be 0 to 0.989, alternatively this ratio may range from 0.15 to 0.989. The ratio of subscript o/(m+n+o) may be up to 0.8, alternatively this ratio may range from 0.01 to 0.8. Subscript y, and at least one of subscripts m and n, may be greater than 0 such that a saccharide component is in a pendant group on the copolymer.

Each subscript a is independently 0, 1, 2, or 3. Alternatively, each subscript a may be 0. When subscript a is 0, then at least one of subscripts m and n is greater than 0, and all of the saccharide components are in pendant groups (not terminal groups) on the copolymer. Each subscript a' may be 0, 1, 2, or 3. Alternatively, each subscript a' may be 0 or 1. When each subscript a' is 0, then subscript o is greater than 0, and the long chain organic groups $R^{1'}$ are pendant groups (not terminal groups) on the copolymer. Subscript y is an integer such that the copolymer has a molecular weight less than 1 million.

Each $R^2$ has formula $Z-(G^1)_b-(G^2)_c$, and there is an average of at least one $R^2$ per copolymer molecule. Group $G^1$ is a saccharide component comprising 5 to 12 carbon atoms. Subscript b or subscript c can be 0. However, a quantity (b+c) has a value ranging from 1 to 10. Group $G^2$ is a saccharide component comprising 5 to 12 carbon atoms additionally substituted with organic or organosilicon groups. Substituted means that a hydrogen atom bonded to a carbon atom has been replaced with another substituent, such as with an organic group or an organosilicon group. Each Z is a linking group.

Each Z is independently selected from the group consisting of: $-R^3-NHC(O)-R^4-$, $-R^3-NHC(O)O-R^4-$, $-R^3-NH-C(O)-NH-R^4-$, $-R^3-C(O)-O-R^4-$, $-R^3-O-R^4-$, $-R^3-CH(OH)-CH_2-O-R^4-$, $-R^3-S-R^4-$, $-R^3-CH(OH)-CH_2-NH-R^4-$, $-R-N(R^1)-R^4-$, $-NHC(O)-R-$, $-NHC(O)O-R-$, $-NH-C(O)-NH-R-$, $-C(O)-O-R-$, $-O-R^4-$, $-CH(OH)-CH_2-O-R^4-$, $-S-R^4-$, $-CH(OH)-CH_2-NH-R^4-$, $-N(R^1)-R^4-$, $-R^3-NHC(O)-$, $-R^3-NHC(O)O-$, $-R^3-NH-C(O)-NH-$, $-R^3-C(O)-O-$, $-R^3-O-$, $-R^3-CH(OH)-CH_2-O-$, $-^3-S-$, $-R^3-CH(OH)-CH_2-NH-$, $-R^3-N(R^1)-$, $-R^3-N(R^8)-C(O)-R^4-$, $-R^3-CH(OH)-CH_2-N(R^8)-R^4-$, or $-R^3-CH(N(R^4)(R^8))CH_2OH$. Alternatively, each Z is independently selected from the group consisting of: $-R^3-N(R^8)-C(O)-R^4-$, $-R^3-CH(OH)-CH_2-N(R^8)-R^4-$, or $-R^3-CH(N(R^4)(R^8))CH_2OH$. Each $R^3$ and each $R^4$ are divalent spacer groups comprising a group of formula $(R^5)_r(R^6)_s(R^7)_t$. At least one of subscripts r, s and t is 1. Each $R^5$ and each $R^7$ are independently an alkylene group of 1 to 12 carbon atoms. Each $R^6$ is $-N(R^8)-$, where $R^8$ is selected from $R^3$, a group of formula Z—X, a monovalent hydrocarbon group, or a reaction product of $-N(H)-$ with an epoxy functional group, a cycloalkylepoxy functional group, a glycidyl ether functional group, an acetic anhydride functional group, or a lactone. Suitable monovalent hydrocarbon groups for $R^8$ may be an alkyl group or an unsaturated hydrocarbon group. When $R^8$ is an unsaturated hydrocarbon group, $R^8$ may be an alkenyl group. The alkenyl group may have 2 to 12 carbon atoms and is exemplified by vinyl, allyl, decenyl, and dodecenyl. Alternatively, the alkenyl group may have a longer chain such as at least 14 carbon atoms. When $R^8$ is a saturated hydrocarbon group, $R^8$ may be an alkyl group. The alkyl group may be relatively short chain, such as 1 to 12 carbon atoms. Alternatively, the alkyl group may have a longer chain, such as at least 14 carbon atoms. Each X is independently a divalent a carboxylic acid, phosphate, sulfate, sulfonate or quaternary ammonium radical. At least one of $R^3$ and $R^4$ must be present in the linking group. Each $R^3$ and each $R^4$ may be the same or different.

Method of Making the Copolymer

The copolymer described above may be made by a method comprising: 1) reacting an organofunctional polyorganosiloxane with a sugar moiety to produce a saccharide siloxane copolymer as described above and 2) removing all or a portion of a solvent, if a solvent is present.

Equilibration/Condensation Reaction

In one embodiment, step 1) is performed by a method comprising two steps. The first step comprises equilibration and/or condensation reaction of
  i) a short chain silanol functional polyorganosiloxane,
  ii) an aminodialkoxyalkylsilane,
  iii) an alkyldialkoxysilane having a long chain organic group ($R^{1'}$) bonded to silicon, and
  iv) an endblocker.

The product of the first step is a long chain organo-modified amino siloxane.

Ingredient (i) may have the formula:

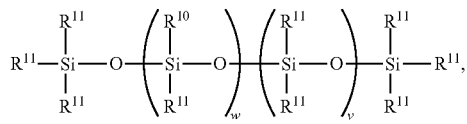

where each $R^{10}$ is a hydroxyl group; each $R^{11}$ is independently a monovalent hydrocarbon group or $R^{10}$; subscript w has a value ranging from 0 to 10,000, alternatively 0 to 50, and subscript v has a value ranging from 0 to 10,000, alternatively 0 to 50, with the proviso that when all instances of $R^{11}$ are monovalent hydrocarbon groups, then subscript w is greater than 0. Alternatively, the short chain silanol functional polyorganosiloxane may be silanol-terminated. Alternatively, the short chain silanol functional polyorganosiloxane may be silanol-terminated and may be free of pendant silanol groups. Ingredient (i) may be a polydimethylsiloxane terminated on both ends with silanol groups and having a DP ranging from 2 to 50, alternatively 2 to 20.

Ingredient (ii) may have the formula $R^{14}R^{13}Si(OR^{12})_2$. Each $R^{12}$ is independently a monovalent hydrocarbon group, such as an alkyl group of 1 to 4 carbon atoms. Each $R^{13}$ is an aminofunctional group such as aminopropyl, aminoethylaminoisobutyl, or aminoethylaminopropyl. Each $R^{14}$ is independently a monovalent hydrocarbon group such as an alkyl group of 1 to 12 carbon atoms, an organic group, or a group of formula $R^3$-Q, where $R^3$ and Q are as described above. Alternatively, each $R^{14}$ is independently a monovalent hydrocarbon group, such as an alkyl group of 1 to 12 carbon atoms, alternatively an alkyl group of 1 to 4 carbon atoms. Ingredient (ii) is exemplified by aminopropyl, methyl, dimethoxysilane; aminoethylaminopropyl, methyl, dimethoxysilane; aminoethylaminoisobutyl, methyl, dimethoxysilane; and combinations thereof.

Ingredient (iii) may have the formula $R^{1'}R^{14}Si(OR^{12})_2$. Each $R^{1'}$, each $R^{12}$, and each $R^{14}$ are as described above. Ingredient (iii) is exemplified by tetradecyl, methyl, dimethoxysilane; hexadecyl, methyl, dimethoxysilane; octadecyl, methyl, dimethoxysilane; eicosyl, methyl, dimethoxysilane; and combinations thereof.

Ingredient (iv) may be a monoalkoxysilane, such as $R^{16}_3SiOR^{15}$. Each $R^{16}$ is a monovalent hydrocarbon group, such as an alkyl group of 1 to 8 carbon atoms or an aryl group. Each $R^{15}$ may be a hydrogen atom or a monovalent hydrocarbon group, such as an alkyl group of 1 to 4 carbon atoms. Alternatively, ingredient (iv) may be a be a polydiorganosiloxane terminated on one end with one silanol group, such as a polydimethylsiloxane terminated on one end with one silanol group. Ingredient (iv) may have the formula

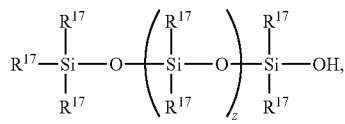

where each $R^{17}$ is independently a monovalent hydrocarbon group, such as an alkyl group of 1 to 8 carbon atoms or an aryl group, and subscript z is an integer from 0 to 10,000, alternatively 0 to 50. One skilled in the art would recognize that during formation of the long chain organo-modified amino siloxane, the stoichiometry can be adjusted such that not all molecules contain an amino group. In this instance, the product of the method is a combination comprising the copolymer described above and a polyorganosiloxane.

In the second step the long chain organo-modified amino siloxane is reacted with a sugar lactone to form the copolymer described above. A sugar lactone (i.e., an aldonolactone or another lactone derived from a saccharide) is reacted with the alkyl modified amino siloxane. The aldonolactone suitable for use in the second step is exemplified by gluconolactone (GL), erythronolactone, galactonolactone, gluconolactone, mannonolactone, and ribolactone. Other lactones derived from saccharides can include glucoronolactone, glucoheptanolactone, glucooctanolactone, isocitric acid lactone, saccharolactone, and lactobionolactone (LBL). Alternatively, the lactone may be GL or LBL. Lactones suitable for use in the second step are commercially available.

Aldonamide Reaction

In an alternative embodiment, the method for making the copolymer comprises:
1) reacting an amine functional polyorganosiloxane containing a primary amine and a secondary amine with a sugar lactone to consume the primary amine,
2) reacting the product of step 1) with a capping agent to block the secondary amine.

Steps 1) and 2) may be performed sequentially. Alternatively, step 1) and step 2) may be combined and performed simultaneously.

The method described above (and the other methods herein in which a secondary amine functional copolymer is formed) may optionally further comprise an additional step. The additional step comprises reacting the secondary amine functionality with a capping agent to block secondary amine functionality. The secondary amine functionality may be selected from aminopropyl, aminoethylaminopropyl, and aminoethylaminoisobutyl. The capping agent may be a lactone, a halogenated unsaturated compound capable of reacting with the hydrogen on the secondary amine functionality, an epoxy functional compound, or an acid anhydride.

The capping agent may be a lactone. The lactone may have the formula:

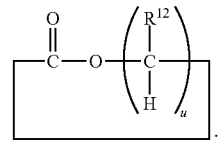

Each $R^{12}$ is independently a hydrogen atom, a hydroxyl group, an alkoxy group, or a saccharide group. Alkoxy groups are exemplified by methoxy, ethoxy, propoxy, and butoxy. Alternatively, each $R^{12}$ is a hydroxyl group or a saccharide group. Subscript u has a value ranging from 5 to 12. The lactone used in step 2) may be exemplified by the sugar lactones described above. Alternatively, the lactone may be butyrolactone, epsilon caprolactone, gamma gluconolactone, delta gluconolactone, and LBL. Alternatively, the lactone may be gamma gluconolactone or delta gluconolactone.

Alternatively, the capping agent may be halogenated unsaturated compound capable of reacting with the hydrogen atom on the secondary amine. The halogenated unsaturated compound may be a halogenated unsaturated hydrocarbon such as an alkenyl chloride. Suitable alkenyl chlorides may have 2 to 12 carbon atoms and may include vinyl chloride, allyl chloride, decyl chloride, or dodecyl chloride.

Alternatively, the capping agent may be an epoxy functional compound. The epoxy functional compound may be selected from allyl epoxy functional compounds, cycloalkylepoxy functional compounds, glycidyl ether functional compounds, and glycidol.

Alternatively, the capping agent may be an acidic anhydride. The acid anhydride may have the formula:

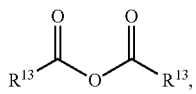

where each $R^{13}$ is independently a monovalent hydrocarbon group. Alternatively, each $R^{13}$ may be an alkyl group, such as an alkyl group of 1 to 12 carbon atoms. Suitable alkyl groups are represented by methyl, ethyl, propyl, and butyl. Alternatively, the acid anhydride may comprise acetic anhydride, chloroacetic anhydride, propionic anhydride, crotonic anhydride, methacrylic anhydride, butyric anhydride, isobutyric anhydride, diethyl pyrocarbonate, or 4-pentenoic anhydride. Alternatively, the acid anhydride may be acetic anhydride.

Epoxy Reactions

Alternatively, the copolymer may be prepared by a method comprising reacting an epoxy functional polyorganosiloxane with an n-alkyl glucamine such as n-methyl glucamine. The epoxy functional polyorganosiloxane may be prepared by methods known in the art, such as by hydrosilylation of ingredients comprising an alkenyl functional epoxy containing compound and a polyorganohydrogensiloxane. The alkenyl functional epoxy containing compound may be allyl glycidyl ether, dodecenyl glycidyl ether, tetradecenyl glycidyl ether, or octadecenylglycidyl ether. The ingredients may optionally further comprise further comprise an alkene, such as undecene. Alternatively, one skilled in the art could react the n-alkyl-glucamine first with the alkenyl functional epoxy containing compound and thereafter perform the hydrosilylation reaction to attach the product thereof to the polyorganohydrogensiloxane.

Alternatively, the copolymer may be prepared by a method comprising:
1) reacting an n-alkyl-glucamine with an alkenyl functional epoxy compound, and
2) hydrosilylating the product of step 1) with a polyorganohydrogensiloxane.

In this method, steps 1) and 2) may be performed sequentially. Alternatively, step 1) and step 2) may be combined and performed simultaneously.

In this method, the alkenyl functional epoxy containing compound may be allyl glycidyl ether, dodecyl glycidyl ether, tetradecyl glycidyl ether, or octadecylglycidyl ether. The n-alkyl glucamine may be n-methyl glucamine.

Each of the methods described above may be performed neat or in the presence of a solvent. The solvent may be an alcohol such as methanol, ethanol, propanol, butanol, or a combination thereof. Alternatively, the organo-functional polyorganosiloxane (e.g., silanol-functional polyorganosiloxane, amine functional polyorganosiloxane, or epoxy functional polyorganosiloxane, or the polyorganohydrogensiloxane) may be dissolved in a solvent such as ethanol with the other ingredients used in the method. All or a portion of the solvent may be removed, for example, by stripping or distillation, after the method is complete. Alternatively, the copolymer may be left in the solvent after the method is complete, for example, if the solvent is a suitable ingredient for an emulsion in which the copolymer will be formulated.

Alternatively, the methods described above may be performed in the presence of an oil. The oil may be added in addition to the solvent. The oil may be added before reacting the ingredients to make the copolymer. Alternatively, the oil may be added during and/or after making the copolymer and before removal of any solvent. Alternatively, the oil may be added after a portion of the solvent is removed. Alternatively, the oil may be added after all of the solvent is removed. When to add the oil may be determined by one of skill in the art depending on which reaction scheme is selected to make the copolymer, the intended end use of the copolymer, and whether the oil selected is reactive with any of the ingredients used in the method. For example, when the oil is, for example, a hydrocarbon such as an alkane, petrolatum, squalane, or mineral oil, the oil may be added earlier in the method because it will not react with the other ingredients used to make the copolymer. When the copolymer will be used as an emulsifier, it may be desirable to add the oil before removing all of the solvent.

The methods described above may be performed by heating. The exact temperature depends on various factors including the specific ingredients selected, however, temperature may range from 50° C. to 100° C. and reaction time for each step may be several hours, alternatively, up to 10 hours, alternatively 1 to 10 hours. The first and second steps in the methods described above may be performed sequentially. Alternatively, the first and second steps may be combined and performed simultaneously.

In the methods described above a molar excess may be used of the functionality on the reagent reacting with the functionality on the polyorganosiloxane. For example, in the hydrosilylation of allyl glycidyl ether with an SiH intermediate polyorganosiloxane, a 1.1:1 ratio is used of the moles allyl glycidyl ether to the moles of SiH. The ratio for the reagent to siloxane bonded functionality may be as large as 1.8:1. Alternatively, the molar ratio may range from 1:1 to 1.8:1, alternatively 1.1:1 to 1.5:1.

Alternatively, the molar ratio of sugar lactone to amine may be 1:1, calculated from amine value of the amine functional polyorganosiloxanes. However, the molar ratio of sugar functionality in the sugar lactone to amine in the amine functional polyorganosiloxane may range from 0.5:1 to 2.0:1.

An exemplary process for making a copolymer described herein comprises mixing the short chain silanol functional polyorganosiloxane with 5 cSt polydimethylsiloxane (DOW CORNING® 200 Fluid), an alkyldialkoxysilane having a long chain organic group ($R^{1'}$) bonded to silicon, and an aminodialkoxyalkylsilane and heating the mixture to 80° C. The resulting reaction mixture may be neutralized with a base such as potassium hydroxide. Water may be added after several hours with additional heating (e.g., at temperatures from 120° C. to 150° C.) for several hours. The resulting reaction mixture may be cooled and neutralized with an acid, such as glacial acetic acid. Volatiles may be removed by vacuum stripping with heating (e.g., at temperatures ranging from 120° C. to 150° C.) for several hours. The resulting product may be filtered to form a long chain organo-modified amino siloxane.

The long chain organo-modified amino siloxane may be reacted with a sugar lactone, such as delta-gluconolactone in the presence of an alcohol by heating at a temperature ranging from 40° C. to 75° C. for several hours. Additional oil may optionally then be added. The resulting mixture may be stripped by heating at a temperature ranging from 40° C. to 74° C., optionally under vacuum.

The methods described above may be performed neat or in the presence of a solvent. The solvent may be a carrier medium suitable for use in personal care composition or a solvent such as that described herein. Alternatively, the method may be performed using as the solvent an alcohol such as ethanol, propanol, butanol, or a combination thereof; and alternatively the solvent may be ethanol or propanol. All or a portion of the solvent may be removed, for example, by stripping or distillation, after the method is complete. Alternatively, the copolymer may be left in the solvent after the method is complete, for example, if the solvent is a suitable carrier medium for a composition in which the copolymer will be formulated.

DEFINITIONS AND USAGE OF TERMS

The art of "personal care" is intended to include any topical treatment of any portion of the body that is intended to provide a benefit to that portion of the body. The a benefit may be direct or indirect, and may be sensory, mechanical, cosmetic, protective, preventative or therapeutic. While it is contemplated that the human body is a particularly desirable target substrate for the presently disclosed personal care compositions and products formulated therefrom, it will be readily apparent to one skilled in the art that other mammals having similar tissues, especially keratinacious tissue such as skin and hair, may be suitable target substrates and that therefore veterinary applications are within the scope of the present invention.

The personal care compositions, as provided, are adapted to provide a benefit to a portion of the body. As used herein, "adapted" means formulated in a manner that permits safe and effective application of the benefit to the portion of the body. As used herein, "safe and effective" means an amount that provides a level of benefit perceivable by a consumer seeking such a benefit without damaging or causing significant discomfort to the consumer seeking such a benefit. A significant discomfort is one that outweighs the benefit provided such that an ordinary consumer will not tolerate it.

A person of ordinary skill in the personal care formulation arts will appreciate the well-known criterion for selecting the essential ingredients, optional additives and excipients, that are suitable according to the intended application of a particular personal care composition. Non-limiting examples of additives which may be formulated into the personal care compositions in addition to the copolymer include: antiperspirants, additional silicones, aerosols, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, anti-dandruff, anti-acne, anti-carie and wound healing-promotion agents.

It is not uncommon for certain benefits to be sacrificed in personal care products formulated to provide multiple benefits in a single product. For instance, with respect to hair, an increase in conditioning benefit is often accompanied by a decrease in hair "body" or volume. Addition of the copolymer may permit the formulation of products which combine such benefits without sacrificing the efficacy of some, and, indeed, in some formulations it provides synergy with respect to the combination of benefits. Personal care products formulated from the personal care compositions comprising the copolymer described herein may provide enhancements in benefits which typically derive from effects which antagonize one another, for example, enhancing both conditioning and curl retention benefits. They also may provide thickening benefits in hair, skin, and color cosmetics.

In addition, the addition of the copolymer described herein to personal care compositions may eliminate or lessen the need for certain other additives. For example, because of the increased hydrogen bonding properties of the copolymer described herein, it is an effective thickening agent for cyclic silicones such as cyclomethicone and may therefore lessen the need for other thickening additives which may incidentally confer undesirable product properties such as stringency, residue formation and/or conditioning defects.

The copolymer described herein may be a gum, waxy solid or solid at ambient conditions. It should be noted, however, that there is a subset of the copolymer that exists in a liquid form, and liquid dispersible forms may also be produced by manipulating conditions such as temperature. However, for some copolymers to achieve a viscosity range that permits ready formation of dispersions, for example solutions or emulsions, the copolymer must first be solubilized by being dissolved in a suitable solvent or solvent blend.

The solubilized copolymer is then used to form a solution or emulsion for ready delivery into the personal care composition. The particular solvent blend is selected based upon the ionic properties of the copolymer, and the suitability of that solvent for the intended application. In one specific embodiment the solvent blend comprises a mixture of paraffin and an alcohol. In a very specific embodiment the alcohol comprises isopropyl alcohol, 2-butyl-octanol, or a combination thereof. Alternatively, the alcohol may comprise 2-butyl-octanol.

The term "dispersion" as used herein means a two-phase system where a first phase comprises finally divided particles distributed throughout a bulk second phase and the first phase constitutes an "internal" or dispersed phase while the second phase constitutes an "external" or continuous phase.

The term "solution" as used herein is intended broadly to include mechanical dispersions, colloidal dispersions and true solutions, and should not be construed as limited to the latter. A solution is a dispersion comprising a uniformly dispersed mixture wherein a first phase constitutes the solute and a second phase constitutes the solvent.

The term "emulsion" as used herein means a dispersion comprising a mixture of two immiscible liquids with the liquid constituting the first, dispersed internal phase being suspended in the second, continuous phase with the aid of an emulsifier.

All amounts, ratios, and percentages are by weight unless otherwise indicated. As used herein, the articles 'a' 'an' and 'the' each refer to one or more, unless otherwise indicated by the context of the application.

Composition

The copolymer described above may be formulated in a composition. The composition comprises (A) a copolymer described above, and (B) an additional ingredient. The additional ingredient depends on the specific copolymer selected and the desired end use for the composition.

The composition may be a personal care composition. The personal care composition may comprise: (i) the copolymer described above, and optionally (ii) a carrier medium suitable to permit topical application of the personal care composition to a portion of the body. The personal care composition is adapted to provide a benefit to the portion of the body to which it is applied. In addition, the personal care composition may optionally comprise (iii) a cross-linker, which acts to cross-link among the copolymer(s) and/or with the substrate to which the composition is applied. The personal care composition may optionally comprise (iv) a surfactant.

Cross-linkers suitable for crosslinking the copolymer are known in the art. In specific embodiments, the crosslinking substantially occurs between the hydroxy-functional groups of the saccharide components. In more specific embodiments the cross-linker may be selected from the following non-limiting list: boric acid, borate ester (e.g., tri-n-propyl borate, triisopropanolamine borate), alkyl boronic acid or ester (e.g., phenyl boronic acid), titanate, (e.g., titanium isopropoxide, diisopropoxytitanium bis(acetylacetonate)), zirconate, glyoxal, glutaraldehyde, epichlorohydrin, urea-formaldehyde, zirconium ammonium carbonate, salt of a multivalent ion, bifunctional epoxy or glycidyl compounds (e.g., 1,4 butanediol diglycidyl ether), di-(N-hydroxymethyl) urea, di-isocyanate (e.g., toluene diisocyanate, hexamethylene diisocyanate), 2-chloro N,N di-ethylacetamide, sodium trimetaphosphate, phosphorous oxychloride, acrolein, N-methyl urea, dicarboxylic acid, bis-acid chloride, dialkyldichlorosilane (e.g., dimethyldichlorosilane), alkyltrichlorosilane (e.g., methyltrichlorosilane), reactive siloxane resin, and combinations thereof. In a very specific embodiment, the cross-linker comprises a reactive siloxane resin or boronic acid or ester.

Alternatively, the copolymer may be delivered to the personal care composition as a dispersion. Diluting or dispersing the copolymer makes it easier to process, and suitably employable solvents include polydimethylsiloxanes, hydrocarbons, and alcohols. Particularly suitable solvents are cyclic siloxanes, hydrocarbon-alcohol mixtures, linear long chain alcohols and branched long chain alcohols, and water.

Due to the compatibility of the copolymer with hydrocarbons, silicones and alcohols, as well as with water, they may be incorporated into both aqueous and non-aqueous based personal care products, which provide a benefit to the portion of the body. In embodiments where the portion of the body comprises hair, the benefit may include increased ease and hold of hair-styling, fixative effects and shine-enhancement.

Emulsions

The copolymer described above was surprisingly found to have improved emulsification properties as compared to some previously known saccharide siloxanes. In one embodiment, the copolymer may be used as an emulsifier. Emulsions made with the copolymer may be useful in personal care applications. The amount of copolymer used as an emulsifier may range from greater than 0 to 10%, alternatively 0 to 5%, and alternatively 1% to 2% in the emulsion.

The copolymer described above was surprisingly found to have improved emulsification properties as compared to some previously known saccharide siloxanes. Therefore, an emulsion including the copolymer as an emulsifier may be prepared. The emulsion may be a water in oil (w/o) emulsion comprising an internal, aqueous phase comprising water and an external, continuous phase comprising an oil and the copolymer as the emulsifier. Without wishing to be bound by theory, it is thought that the emulsion need not further comprise any surfactant other than the copolymer to maintain the dispersion of the internal phase.

The oil used in the continuous phase of the emulsion may be a silicone oil or an organic oil. The oil may be a silicone oil such as a polydialkylsiloxane having a viscosity of 1 to 350 cSt. Such silicone oils are commercially available as DOW CORNING® 200 Fluids with viscosities ranging from 2 centiStokes (cSt) to 350 cSt, and DOW CORNING® FZ-3196, DOW CORNING® 244 Fluid, and DOW CORNING® 245 Fluid from Dow Corning Corporation of Midland, Mich., U.S.A. Dimethicone oils from Dow Corning Corporation include 244 Fluid, 245 Fluid, and 200 Fluids with viscosity of 2 cSt, 5 cSt, 10 cSt 20 cSt, 50 cSt, 100 cSt, or 350 cSt.

Alternatively, certain organic oils are suitable for use in the emulsion. Suitable organic oils include esters, vegetable and/or mineral oils, hydrocarbon oils, or fatty alcohols.

Suitable esters include isopropyl myristate, octyl octanonanoate, decyl oleate, isopropyl palmitate, glyceryl stearate, ethylhexyl stearate, isopropyl isostearate, C12-C15 alkyl benzoate, octyl cocoate, octyl palmitate, myristyl lactate, and dioctyl adipate. Examples of esters further comprise cetyl ethylhexanoate (which is commercially available as Schercemol™ CO Ester from The Lubrizol Corporation of Wickliffe, Ohio, U.S.A.) and triethylhexanoin (which is commercially available as Schercemol™ GTO Ester, also from Lubrizol).

Suitable vegetable and mineral oils include almond oil, apricot kernel, avocado oil, castor oil, evening primrose, jojoba oil, sunflower oil, olive oil, wheat germ oil, and mineral oil.

Suitable hyrocarbon oils include petrolatum, mineral oil, squalene, capric/caprylic triglyceride; an alkane of at least 12 carbon atoms. For example, long chain alkanes (e.g., alkanes having at least 12 carbon atoms, such as isododecane or isohexadecane) may be used as the organic oil.

Suitable fatty alcohols that include strearyl alcohol, cetyl alcohol.

The emulsion may be prepared by a method comprising dispersing the copolymer described above in an oil and thereafter adding the aqueous phase. The aqueous phase may be added to the oil phase in increments with mixing between additions. The resulting combination of aqueous and oil phases may be subjected to high shear. The oil forms the external or continuous phase. Mixing may be performed, for example, by mixing with a cross stirrer at 700 to 1,000 revolutions per minute (rpm) while adding the aqueous phase. After the aqueous phase has been added, the resulting mixture may optionally be further mixed at 1,000 to 2,000 rpm for a period of time such as 1 second to 10 minutes, alternatively 1 minute to 5 minutes. For example, mixing conditions after all the aqueous phase have been added may include mixing for 1 minute at 1,000 rpm and then 5 minutes at 2,000 rpm.

The high shear mixing may be performed using special equipment, which allows to the emulsion mix at very high shear to reduce particle size and increase the viscosity of the emulsion. High shear mixing may improve stability of the emulsion. The high shear mixing may be performed with a commercially available high shear device, e.g., a homogenizer such as a T25 Digital ULTRA-TURRAX® commercially available from IKA of Wilmington, N.C., U.S.A. or a homogenizer such as L4RT commercially available from Silverson Machines Ltd. of England. The exact conditions for high shear mixing will vary depending on factors such as the initial viscosity of the emulsion, however, high shear conditions are exemplified by mixing the emulsion at 7,000 to 8,000 rpm for 1 second to 1 minute, alternatively 15 seconds.

It will be understood by one of ordinary skill in the art that there is a continuum for the ease with which a desired emulsion forms. The emulsions described herein share similar constraints with other emulsions. That is, they are thermodynamically unstable and need an input of energy to initiate emulsification. Simple agitation via mixing may be sufficient, or higher shear means including the employment of high shear devices may be used. Alternatively, an inversion method may be used.

A degree of agitation necessary to form the emulsion may require employment of mixing devices. Mixing devices typically provide the required energy input. Non-limiting examples of these mixing devices spanning the shear range include: 1) a vessel with an impeller, for example, propeller, pitched blade impeller, straight blade impeller, Rushton impeller, or Cowles blade; 2) kneading type mixers, for example, Baker-Perkins; 3) high shear devices which use positive displacement through an orifice to generate shear, for example, homogenizer, sonolator, or microfluidizer; 4) high shear devices using a rotor and stator configuration, for example, colloid mills, homomic line mills, homogenizers from IKA, or Bematek; 5) continuous compounders with single or dual screws; 6) change can mixers with internal impellers or rotor/stator devices, for example, Turello mixer; and 7) centrifugal mixers, for example, Hauschild speedmixers. Combinations of mixing devices can also provide benefits, for example a vessel with an impeller can be connected to a high shear device. High shear devices are known in the art and are commercially available, for example, the high shear device may be a homogenizer such as a T25 Digital ULTRA-TURRAX® commercially available from IKA of Wilmington, N.C., U.S.A. or high shear mixer from Silverson Machines Ltd. of England.

The choice of mixing device is based on the type of internal phase to be emulsified. For example, low viscosity internal phases can be emulsified using high shear devices which use positive displacement through an orifice. However, in the case of high viscosity internal phases, a rotor/stator device, twin screw compounder or change can mixer are often better choices.

The order of ingredient addition in the preparation of the emulsion may be determined empirically. For example, a desirable order of addition for a thick-phase emulsification may be: (a) combine the copolymer with an oil; (b) add aqueous phase comprising water in increments with shear until a thick phase emulsion forms; and optionally (c) further dilute with additional oil and/or further oil phase to a desired concentration, with shear. The method may optionally further comprise adding an additional ingredient, such as those described below Emulsions made with the copolymer may be useful in personal care products. Therefore, the method may optionally further comprise formulating a personal care product with the emulsion. The personal care products may be functional with respect to the portion of the body to which they are applied, cosmetic, therapeutic, or some combination thereof. Conventional examples of such products include, but are not limited to: antiperspirants and deodorants, skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, wrinkle fillers, skin imperfection hiders, skin surface smoothers, eyelash curlers, nail varnishes, hair make-up products, eye shadows, body makeups, and powders, medicament creams, pastes or sprays including anti-acne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

In a specific embodiment, water in oil emulsion samples were prepared according to the following general procedure. The oil phase was prepared by mixing an emulsifier with an oil. The oil was isopropyl myristate or DOW CORNING® 200 Fluid, a silicone oil with a viscosity of 5 cSt, which is commercially available from Dow Corning Corporation. The emulsifier was a copolymer as described above. In each oil phase, the oil phase contained 10% emulsifier and 90% oil. The aqueous phase was prepared by mixing water and sodium chloride in a water:NaCl weight ratio ranging from 39:1 to 99:1. Alternatively, the aqueous phase may comprise water, sodium chloride, and glycerol in a weight ratio (water:NaCl: glycerol) of 74:1:5 to 92.5:1.25:6.25. For each sample, the aqueous phase was added to the oil phase in increments. Between the addition of each increment, the sample was mixed for a period of time at 3400 revolutions per minute (rpm) in a DAC150 FlackTek™ SpeedMixer™ (commercially available from FlackTek, Inc. of Landrum, S.C., U.S.A.) to provide a coarse emulsion.

After all the aqueous phase was added, the resulting coarse emulsion was subjected to shear at ≥7,000 rpm in a homogenizer (T25 Digital ULTRA-TURRAX® commercially available from IKA of Wilmington, N.C., U.S.A.) to provide a fine emulsion The aqueous phase may be present in an amount ranging from 20% to 95%, alternatively 40 to 90%, and alternatively 60% to 80% by weight based on the weight of the emulsion.

Personal Care Applications

The emulsion described above is useful in personal care applications. When the emulsion described above is used in personal care applications, the emulsion may further comprise an additional ingredient, such as those described above. The additional ingredient may be selected from additional silicones, aerosols, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, antiperspirants, anti-dandruff, anti-acne, anti-carie and wound healing-promotion agents, an additional oil, a hydrophilic medium, a filler, a fiber, a film forming polymer, an additional surfactant and/or emulsifier, a dyestuff, a structuring agent, an active ingredient, a fragrance, a preservative, and combinations thereof. Alternatively, the additional ingredient can be selected from an additional oil, a hydrophilic medium, a filler, a fiber, a film forming polymer, an additional surfactant and/ or emulsifier, a dyestuff, a structuring agent, an active ingredient (such as a personal care active), a fragrance, a preservative, or a combination thereof.

Additional Oil

The additional oil may be another oil selected from the oils as described above, or the oil may be chosen from hydrocarbon-based oils, silicone oils and fluorinated oils. The oil may be chosen from volatile oils and non volatile oils, and mixtures thereof.

For purposes of this application, the term "hydrocarbon-based oil" means an oil formed essentially from, or even consisting of, carbon and hydrogen atoms, and possibly oxygen and nitrogen atoms, and containing no silicon or fluorine atoms; it may contain ester, ether, amine, or amide groups.

For purposes of this application, the term "silicone oil" means an oil containing at least one silicon atom, and alternatively containing $\equiv$Si—O— groups.

For purposes of this application, the term "fluorinated oil" means an oil containing at least one fluorine atom.

For purposes of this application, the term "volatile oil" means an oil (or non-aqueous medium) capable of evaporating on contact with the skin in less than one hour, at room temperature and atmospheric pressure. The volatile oil may be a volatile cosmetic oil, which is liquid at room temperature, especially having a non-zero vapor pressure, at room temperature and atmospheric pressure, in particular having a vapor pressure ranging from 0.13 Pa to 40 000 Pa (10~3 to 300 mmHg), alternatively ranging from 1.3 Pa to 13 000 Pa (0.01 to 100 mmHg) and alternatively ranging from 1.3 Pa to 1300 Pa (0.01 to 10 mmHg).

In addition, the volatile oil generally has a boiling point, measured at atmospheric pressure, ranging from 150° C. to 260° C. and alternatively ranging from 170° C. to 250° C.

The emulsion may comprise a volatile hydrocarbon-based oil chosen especially from hydrocarbon-based oils with a flash point ranging from 40° C. to 102° C., alternatively ranging from 40° C. to 55° C. and alternatively ranging from 40° C. to 50° C.

The volatile oil may be present in the emulsion in an amount ranging from 0.1% to 80% by weight, alternatively ranging from 1% to 70% by weight, and alternatively ranging from 5% to 50% by weight, relative to the total weight of the emulsion.

The emulsion may comprise at least one non-volatile oil in a non-volatile liquid fatty phase. The non-volatile oil may be present in an amount ranging from 0.1% to 80% by weight, alternatively ranging from 0.5% to 60% by weight, and alternatively ranging from 1% to 50% by weight relative to the total weight of the non-volatile liquid fatty phase.

The volatile hydrocarbon-based oils may be selected from hydrocarbon-based oils containing from 8 to 16 carbon atoms, and especially branched C8-C16 alkanes, for instance C8-C16 isoalkanes of petroleum origin (also known as isoparaffins), for instance isododecane (also known as 2,2,4,4, 6-pentamethylheptane), isodecane and isohexadecane, for example the oils sold under the trade names Isopar or Permethyl, branched C8-C16 esters and isohexyl neopentanoate, and combinations thereof.

Volatile oils that may also be used include volatile silicones, for instance volatile linear or cyclic silicone oils, especially those with a viscosity $\leq$8 centistokes ($8\times10^6$ m$^2$/s) and especially containing from 2 to 7 silicon atoms, these silicones optionally comprising alkyl or alkoxy groups containing from 1 to 10 carbon atoms.

Volatile fluorinated solvents such as nonafluoro-methoxybutane or perfluoromethylcyclopentane are also suitable for use in the composition.

Non-volatile hydrocarbon-based oils include, but are not limited to, hydrocarbon-based oils of plant origin, such as triesters of fatty acids and of glycerol, the fatty acids of which may have varied chain lengths from 4 to 24 carbon atoms, these chains possibly being linear or branched, and saturated or unsaturated. These oils are exemplified by wheat germ oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil or musk rose oil; or caprylic and/or capric acid triglycerides; synthetic ethers containing from 10 to 40 carbon atoms; apolar hydrocarbon-based oils, for instance squalene, linear or branched hydrocarbons such as liquid paraffin, liquid petroleum jelly and naphthalene oil, hydrogenated or partially hydrogenated polyisobutene, isoeicosane, squalane, decene/butene copolymers and polybutene/polyisobutene copolymers, and polydecenes, and mixtures thereof; synthetic esters, for instance oils of formula R'COOR" in which R' represents a linear or branched fatty acid residue containing from 1 to 40 carbon atoms and R" represents a hydrocarbon-based chain, which is especially branched, containing from 1 to 40 carbon atoms, on condition that R'+R">10, for instance cetostearyl octanoate, isopropyl myristate, isopropyl palmitate, alkyl benzoates of 12 to 15 carbon atoms, hexyl laurate, diisopropyl adipate, isononyl isononanoate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate or diisostearyl malate; and pentaerythritol esters; fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpenta-decanol; higher fatty acids such as oleic acid, linoleic acid or linolenic acid; carbonates; acetates; citrates; and combinations thereof.

The non-volatile silicone oils may be: non-volatile polydimethylsiloxanes (PDMS); polydimethylsiloxanes comprising alkyl or alkoxy groups, which are pendent and/or at the end of a silicone chain, these groups each containing from 3 to 40 carbon atoms; phenylsilicones; optionally fluorinated polyalkylmethylsiloxanes; polysiloxanes modified with fatty acids, fatty alcohols or polyoxyalkylenes, and combinations thereof. Alkylmethylsiloxanes, which generally will have the formula Me$_3$SiO[Me$_2$SiO]$_A$[MeR'"SiO]$_B$SiMe$_3$, in which R'" is a hydrocarbon group containing 6 to 30 carbon atoms, Me represents methyl, and the degree of polymerization (DP), i.e., the sum of A and B ranges from 3 to 50. Both the volatile and liquid species of alkymethysiloxanes can be used in the composition.

The oil may alternatively comprise a silicone carbinol. These materials are described in WO 03/101412 A2, and can be commonly described as substituted hydrocarbyl functional siloxane fluids or resins.

The emulsion may contain an oil with a molar mass ranging from 650 to 10,000 g/mol, which may be selected from: lipophilic polymers such as polybutylenes; polyisobutylenes, for example hydrogenated polyisobutylenes; polydecenes and hydrogenated polydecenes; vinylpyrrolidone copolymers such as a vinylpyrrolidone/1-hexadecene copolymer (MM=7300 g/mol); esters such as linear fatty acid esters with a total carbon number ranging from 35 to 70, for instance pentaerythrityl tetrapelargonate; hydroxylated esters such as polyglyceryl-2 triisostearate; aromatic esters such as tridecyl trimellitate; and pentaerythritol esters, and triisoarachidyl citrate, pentaerythrityl tetraisononanoate, glyceryl triisostearate, glyceryl tris (2-decyl) tetradecanoate, pentaerythrityl tetraisostearate, polyglyceryl-2 tetraisostearate, and combinations thereof.

The emulsion may comprise a fluid silicone compound such as a silicone gum or a silicone oil of high viscosity.

A polydimethylsiloxane with a viscosity at 25° C. ranging from 10 to 10,000,000 cSt., alternatively 1,000 to 2,500,000 cSt., alternatively 5,000 to 1,000,000 cSt., and alternatively 10,000 to 60,000 cSt. may be selected.

The weight-average molecular mass of the fluid silicone may range from 1,000 to 1,500,000 g/mol, alternatively 200,000 to 1,000,000 g/mol.

The oil phase of the emulsion can also contain silicone elastomer gels, elastomeric solid organopolysiloxane enclosed in a fatty phase, where at least one elastomeric solid organopolysiloxane is at least partially crosslinked. Examples of such elastomeric solid organopolysiloxane are described in the following Patents and Patent Publications U.S. Pat. No. 5,654,362, EP 848029, EP 869142, WO2007109240, WO2007109260, WO2007109282, WO2009006091, WO2010080755, U.S. Pat. No. 4,987,169, and U.S. Pat. No. 5,760,116. These elastomer gels can be non emulsifying or self emulsifying or a combination of both.

Hydrophilic Medium

The aqueous phase of the emulsion may comprise a hydrophilic medium comprising water or a mixture of water and a hydrophilic organic solvent, for instance alcohols, such as linear or branched lower monoalcohols containing from 2 to 5 carbon atoms, for instance ethanol, isopropanol or n-propanol, and polyols, for instance glycerol, diglycerol, propylene glycol, sorbitol, pentylene glycol and polyethylene glycols, or alternatively hydrophilic C2 ethers and C2-C4 aldehydes.

The water or the mixture of water and of hydrophilic organic solvents may be present in the emulsion in an amount ranging from 0.1% to 95% by weight and alternatively ranging from 10% to 80% by weight relative to the total weight of the emulsion.

Fillers

The filler suitable for use in the emulsion described herein may be mineral or organic, of any form, platelet-shaped, spherical or oblong, irrespective of the crystallographic form (for example lamellar, cubic, hexagonal, orthorhombic, etc.). Examples include talc, mica, silica, kaolin, polyamide, poly-β-alanine powder and polyethylene powder, tetrafluoroethylene polymer powders, lauroyllysine, starch, boron nitride, hollow polymer microspheres, acrylic acid copolymers, silicone resin microbeads, elastomeric polyorganosiloxane particles, precipitated calcium carbonate, magnesium carbonate, magnesium hydrogen carbonate, hydroxyapatite, hollow silica microspheres, glass or ceramic microcapsules, and metal soaps for example zinc stearate, magnesium stearate, lithium stearate, zinc laurate or magnesium myristate, polymethyl methacrylate powders. Alternatively, the filler may be a polyurethane powder.

Alternatively, the filler may be an elastomeric organopolysiloxane powder. Advantageously, the elastomeric organopolysiloxane is non-emulsifying. Spherical elastomeric organopolysiloxanes are described in patent applications JP-A-61-194 009, EP-A-242 219, EP-A-295 886 and EP-A-765 656. The organopolysiloxane powders can also mixed with other particles as described in patent publication U.S. Pat. No. 7,399,803.

The elastomeric organopolysiloxane powder may comprise at least one elastomeric organopolysiloxane powder coated with silicone resin, such as with silsesquioxane resin, as described, for example, in patent U.S. Pat. No. 5,538,793.

Other elastomeric organopolysiloxanes in the form of spherical powders may be hybrid silicone powders functionalized with fluoroalkyl groups or hybrid silicone powders functionalized with phenyl groups.

The filler may be an N-acylamino acid powder. The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The amino acid may be, for example, lysine, glutamic acid or alanine.

When present, the filler may be added to the emulsion in an amount ranging from 0.01% to 30% by weight.

Fibers

For purposes of this application, the term "fiber" means an object of length L and diameter D such that L is very much greater than D, D being the diameter of the circle in which the cross section of the fiber is inscribed.

In particular, the ratio L/D (or shape factor) ranges from 3.5 to 2500, alternatively 5 to 500, and alternatively 5 to 150.

The fiber that may be used in the emulsion may be fibers of synthetic or natural, mineral or organic origin. The fiber that may be used in the emulsion may be selected from polyamide, cellulose, poly-p-phenylene-terephthamide or polyethylene fibers. Polyethylene fibers may also be used.

The fibers may be present in the emulsion in an amount ranging from 0.01% to 10% by weight.

Film-Forming Polymer

Certain film-forming polymers may be gelling agents. For the purposes of this application, the term "film-forming polymer" means a compound containing at least two repeating units and alternatively at least three repeating units, where said compound is capable, by itself or in the presence of an auxiliary film-forming agent, of forming a macroscopically continuous film on a support, especially on keratin materials, alternatively a cohesive film and alternatively a film with cohesion and mechanical properties such that said film can be isolated from said support.

In one embodiment, the film-forming polymer is a film forming organic polymer chosen from the group comprising: film-forming polymers that are soluble in an organic liquid medium, in particular liposoluble polymers, when the organic liquid medium comprises at least one oil; film-forming polymers that are dispersible in an organic solvent medium, in particular polymers in the form of non-aqueous dispersions of polymer particles, preferably dispersions in silicone oils or hydrocarbon-based oils.

Alternatively, the film-forming polymers that may be used in the emulsion may include synthetic polymers, of free-radical type or of polycondensate type, polymers of natural origin, and mixtures thereof. Such film-forming polymers include acrylic polymers, polyurethanes, polyesters, polyamides, polyureas, cellulose-based polymers, for instance nitrocellulose, silicone polymers, in particular silicone resins, silicone-grafted acrylic polymers, polyamide polymers and copolymers, and polyisoprenes.

The composition according to the invention may comprise, as film-forming polymer, a dispersion of particles of a grafted ethylenic polymer in the fatty phase.

Silicone-based macromonomers that may be used as the film forming polymer include polydimethylsiloxanes containing mono(meth)acrylate end groups. Silicone-based macromonomers that may be used include monomethacryloxypropyl polydimethylsiloxanes.

Alternatively, the emulsion may contain, as film-forming polymer, a linear block ethylenic polymer, referred to hereinbelow as a "block polymer". For purposes of this application, the term "block polymer" means a polymer comprising at least two different blocks and preferably at least three different blocks.

The polymer may be a polymer of linear structure. Alternatively, a polymer of non-linear structure is, for example, a polymer of branched, star, grafted or other structure may be used.

In one embodiment, the film forming polymer polymer comprises at least three different blocks, and the first and second blocks of the block polymer are mutually incompatible.

In one embodiment, the film-forming polymer is an organic film-forming polymer that is soluble in the fatty phase, which comprises a liquid phase comprising at least one oil.

The liposoluble film forming polymer may be of any chemical type and may especially be chosen from: a) liposoluble, amorphous homopolymers and copolymers of olefins, of cycloolefins, of butadiene, of isoprene, of styrene, of vinyl ethers, esters or amides, or of (meth) acrylic acid esters or amides comprising a linear, branched or cyclic alkyl group of 4 to 50 carbon atoms, and which may be amorphous. The liposoluble homopolymers and copolymers may be obtained from monomers selected from the group consisting of isooctyl (meth) acrylate, isononyl (meth) acrylate, 2-ethylhexyl (meth) acrylate, lauryl (meth) acrylate, isopentyl (meth) acrylate, n-butyl (meth) acrylate, isobutyl (meth) acrylate, methyl (meth) acrylate, tert-butyl (meth) acrylate, tridecyl (meth) acrylate and stearyl (meth) acrylate, or combinations thereof.

Particular liposoluble copolymers that may be used include: i) acrylic-silicone grafted polymers containing a silicone backbone and acrylic grafts or containing an acrylic backbone and silicone grafts, such as the product sold under the name SA 70.5 by 3M and described in patents U.S. Pat. No. 5,725,882; U.S. Pat. No. 5,209,924; U.S. Pat. No. 4,972,037; U.S. Pat. No. 4,981,903; U.S. Pat. No. 4,981,902 and U.S. Pat. No. 5,468,477, and in patents U.S. Pat. No. 5,219,560 and EP 0 388 582; ii) liposoluble polymers bearing fluoro groups, belonging to one of the classes described above, in particular the Fomblin products described in patent U.S. Pat. No. 5,948,393 and the alkyl (meth) acrylate/perfluoroalkyl (meth) acrylate copolymers described in patents EP 0 815 836 and U.S. Pat. No. 5,849,318; iii) polymers or copolymers resulting from the polymerization or copolymerization of an ethylenic monomer, comprising one or more ethylenic bonds, which may be conjugated (or dienes). A s polymers or copolymers resulting from the polymerization or copolymerization of an ethylenic monomer, it is possible to use vinyl, acrylic or methacrylic copolymers.

In one embodiment, the film-forming polymer is a block copolymer comprising at least one block consisting of styrene units or styrene derivatives (for example methylstyrene, chlorostyrene or chloromethylstyrene).

In one embodiment, the film-forming polymer is selected from copolymers of a vinyl ester (the vinyl group being directly attached to the oxygen atom of the ester group and the vinyl ester having a saturated, linear or branched hydrocarbon-based radical of 1 to 19 carbon atoms, linked to the carbonyl of the ester group) and of at least one other monomer, which may be a vinyl ester (other than the vinyl ester already present), an α-olefin (containing from 8 to 28 carbon atoms), an alkyl vinyl ether (the alkyl group of which contains from 2 to 18 carbon atoms) or an allylic or methallylic ester (containing a saturated, linear or branched hydrocarbon-based radical of 1 to 19 carbon atoms, linked to the carbonyl of the ester group).

These copolymers may be partially crosslinked using crosslinking agents, which may be either of the vinyl type or of the allylic or methallylic type, such as tetraallyloxyethane, divinylbenzene, divinyl octanedioate, divinyl dodecanedioate, and divinyl octadecanedioate.

Liposoluble film-forming polymers that may also be mentioned include liposoluble copolymers, such as those resulting from the copolymerization of vinyl esters containing from 9 to 22 carbon atoms or of alkyl acrylates or methacrylates, the alkyl radicals containing from 10 to 20 carbon atoms.

Such liposoluble copolymers may be selected from copolymers of polyvinyl stearate, polyvinyl stearate crosslinked with divinylbenzene, with diallyl ether or with diallyl phthalate, polystearyl (meth) acrylate copolymers, polyvinyl laurate and polylauryl (meth) acrylate copolymers, these poly (meth) acrylates possibly being crosslinked with ethylene glycol dimethacrylate or tetraethylene glycol dimethacrylate.

Amorphous and liposoluble polycondensates, preferably not comprising any groups donating hydrogen interactions, in particular aliphatic polyesters containing C4-50 alkyl side chains or polyesters resulting from the condensation of fatty acid dimers, or even polyesters comprising a silicone-based segment in the form of a block, graft or end group, as defined in patent application FR 0 113 920.

Amorphous and liposoluble polysaccharides comprising alkyl (ether or ester) side chains, in particular alkylcelluloses containing a saturated or unsaturated, linear or branched C1 to C8 alkyl radical, such as ethylcellulose and propylcellulose.

Alternatively, the film-forming polymer may be selected from cellulose-based polymers such as nitrocellulose, cellulose acetate, cellulose acetobutyrate, cellulose acetopropionate or ethylcellulose, or from polyurethanes, acrylic polymers, vinyl polymers, poly vinyl butyrals, alkyd resins, resins derived from aldehyde condensation products, such as arylsulfonamide-formaldehyde resins, for instance toluene-sulfonamide-formaldehyde resin, and aryl sulfonamide epoxy resins.

Alternatively, the film forming polymer may be a silicone resin. For purposes of this application, the term "resin" means a three-dimensional structure. In one embodiment, the silicone resin is selected from silsesquioxanes and siloxysilicates. In one embodiment, the silicone resin is selected from siloxysilicates, such as trimethyl siloxysilicates, which are represented by the following formula: $[R^{16}_3SiO_{1/2}]_E$ $(SiO_{4/2})_F$ (units M and Q), in which subscripts E and F may each independently have values ranging from 50 to 80, and $R^{16}$ represents an alkyl, such as a methyl or an alkyl of two or more carbon atoms. The ratio of the units M to the units Q may range from 0.7 to 1.

Alternatively, the silicone resin may be selected from silsesquioxanes comprising T units of formula: $[R^{17}SiO_{3/2}]_G$, in which subscript G has a value that may range up to several thousand and $R^{17}$ represents an alkyl, such as a methyl or an alkyl of two or more carbon atoms. In one embodiment, the silsesquioxane is selected from polymethylsilsesquioxanes, which are silsesquioxanes such that $R^{17}$ is a methyl group or a propyl group (polypropylsilsesquioxane). The polymethylsilsesquioxanes may comprise, for example, less than 500 T units, and alternatively 50 to 500 T units.

In one embodiment of the invention, the silicone resin is soluble or dispersible in silicone oils or volatile organic liquids. In one embodiment, the silicone resin is solid at 25° C.

In one embodiment, the silicone resin may have a molecular mass ranging from 1,000 to 10,000 grams/mol.

In another embodiment, the film-forming silicone resin is a copolymer, in which at least one unit of the copolymer is chosen from the silicone units M, D, T and Q, and in which at least one additional unit of the copolymer is chosen from esters.

In a non-limiting manner, the film-forming polymers may be chosen from the following polymers or copolymers: polyurethanes, polyurethane-acrylics, polyureas, polyurea-polyurethanes, polyester-polyure thanes, polyether-polyurethanes, polyesters, polyesteramides, alkyds; acrylic and/or vinyl polymers or copolymers; acrylic-silicone copolymers; polyacrylamides; silicone polymers, for instance silicone polyurethanes or silicone acrylics, and fluoro polymers, and mixtures thereof.

The film forming polymer may be a vinyl polymer comprising at least one carbosiloxane dendrimer-based unit. The vinyl polymer may especially have a backbone and at least one side chain, which comprises a carbosiloxane dendrimer structure. For purposes of this application, the term "carbosiloxane dendrimer structure" represents a molecular structure with branched groups of high molecular masses with high regularity in the radial direction starting from the backbone bond. Such carbosiloxane dendrimer structures are described in the form of a highly branched siloxane-silylalkylene copolymer in the laid-open Japanese patent application Kokai 9-171154.

The vinyl polymer may be one of the polymers described in the examples of patent application EP 0 963 751, or a polymer obtained according to the process described in the said patent application.

According to one embodiment, the vinyl polymer may further comprise at least one organofluorine group. The fluoro vinyl polymer may be one of the polymers described in the examples of patent application WO 03/045 337, or one of polymers obtained according to the process described in said patent application.

According to one embodiment, the grafted vinyl polymers are borne in an oil, which is may be volatile, selected from silicone oils and/or hydrocarbon-based oils. According to one embodiment, the silicone oil may be cyclopentasiloxane. Alternatively, the hydrocarbon-based oil may be isododecane. The emulsion may comprise at least one polyamide polymer or copolymer, which may be selected from polyamide homopolymers, polyamides branched with fatty chains, polyamide-organosiloxanes, polyamide-polyester copolymers and polyamide-polyacrylic copolymers, and mixtures thereof.

As polyamide polymers that may be used in the emulsion, mention may also be made of polyamides comprising at least one polyorganosiloxane group, containing 1 to 1,000 organosiloxane units in the main chain or in the form of a graft. The polyamide polymers are, for example, those described in documents U.S. Pat. No. 5,874,069, U.S. Pat. No. 5,919,444, U.S. Pat. No. 6,051,216, U.S. Pat. No. 5,981,680 and WO 04/054 524.

The emulsion may comprise a semi-crystalline polymer, which may have a melting point of greater than or equal to 30° C. The melting point values correspond to the melting point measured using a differential scanning calorimeter (DSC) such as the calorimeter sold under the name DSC 30 by Mettler, with a temperature rise of 5 or 10° C. per minute. (The melting point considered is the point corresponding to the temperature of the most endothermic peak in the thermogram). The semi-crystalline polymer comprises at least one crystallizable pendent chain or at least one crystallizable block. Aside from the crystallizable chains or blocks, the polymer blocks are amorphous. For the purposes of the invention, the term "crystallizable chain or block" means a chain or block which, if it was alone, would change from the amorphous state to the crystalline state reversibly, depending on whether it is above or below the melting point. For the purposes of this application, a chain is a group of atoms that are pendent or lateral relative to the polymer backbone. A block is a group of atoms belonging to the backbone, this group constituting one of the repeating units of the polymer. The semi-crystalline polymers that may be used in the invention are exemplified by polyolefin block copolymers of controlled crystallization, the monomers of which are described in EP-A-0 951 897.

The film forming polymer, when present, may be in the emulsion in an amount ranging from 0.1% to 30% by weight.

Additional Surfactants/Emulsifiers

The emulsion may further comprise an additional surfactant or emulsifier. The additional surfactant or emulsifier may be solid at room temperature, which may be a block polymer, a grafted polymer and/or a random polymer, alone or in combination of two or more. Among the grafted polymers that may be mentioned are silicone polymers grafted with a hydrocarbon-based chain and hydrocarbon-based polymers grafted with a silicone chain.

Thus, grafted-block or block copolymers comprising at least one block of polyorganosiloxane type and at least one block of a free-radical polymer, for instance grafted copolymers of acrylic/silicone type, may be used, which may be used especially when the non-aqueous medium contains silicone.

It is also possible to use grafted-block or block copolymers comprising at least one block of polyorganosiloxane type and at least one block of a polyether. The polyorganopolysiloxane block may be a polydimethylsiloxane or a poly (C2-C18) alkylmethylsiloxane; the polyether block may be a poly (C2-C18) alkylene, such as polyoxyethylene and/or polyoxypropylene. In particular, dimethicone copolyols or (C2-C18) alkyldimethicone copolyols may be used.

Water soluble or water dispersible silicone polyether compositions may be included in the present emulsions. These are also known as polyalkylene oxide silicone copolymers, silicone poly (oxyalkylene) copolymers, silicone glycol copolymers, or silicone surfactants. These can be linear, rake, or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible. Another type of silicone polyether composition that may be included in the present composition is an ABn polyalkylene oxide silicone copolymers as described in EP 0 492 657.

The additional emulsifier or surfactant may be selected from nonionic, anionic, cationic and amphoteric surfactants or combinations thereof. Reference may be made to Kirk-Othmer's "Encyclopedia of Chemical Technology", volume 22, pp. 333-432, 3rd edition, 1979, Wiley, for the definition of the properties and (emulsifying) functions of surfactants, in particular pp. 347-377 of this reference, for anionic, amphoteric and nonionic surfactants.

Nonionic surfactants may be comprise: oxyethylenated and/or oxypropylenated ethers (which may comprise from 1 to 150 oxyethylene and/or oxypropylene groups) of glycerol; oxyethylenated and/or oxypropylenated ethers (which may comprise from 1 to 150 oxyethylene and/or oxypropylene groups) of fatty alcohols (especially of a C8-C24 and alternatively C12-C18 alcohol), such as oxyethylenated cetearyl alcohol ether containing 30 oxyethylene groups (CTFA name Ceteareth-30) and the oxyethylenated ether of the mixture of C12-C15 fatty alcohols comprising 7 oxyethylene groups (CTFA name C12-15 Pareth-7); fatty acid esters (such as a C8-C24 and alternatively C16-C22 acid) of polyethylene glycol (which may comprise from 1 to 150 ethylene glycol units), such as PEG-50 stearate and PEG-40 monostearate; fatty acid esters (especially of a C8-C24 and preferably C16-C22 acid) of oxyethylenated and/or oxypropylenated glyceryl ethers (which may comprise from 1 to 150 oxyethylene and/or oxypropylene groups), for instance PEG-200 glyceryl monostearate; glyceryl stearate polyethoxylated with 30 ethylene oxide groups, glyceryl oleate polyethoxylated with 30 ethylene oxide groups, glyceryl cocoate polyethoxylated with 30 ethylene oxide groups, glyceryl isostearate polyethoxylated with 30 ethylene oxide groups, and glyceryl laurate polyethoxylated with 30 ethylene oxide groups; fatty acid esters (especially of a C8-C24 and preferably C16-C22 acid) of oxyethylenated and/or oxypropylenated sorbitol ethers (which may comprise from 1 to 150 oxyethylene and/or oxypropylene groups); dimethicone copolyol benzoate; copolymers of propylene oxide and of ethylene oxide, also known as EO/PO polycondensates; and mixtures thereof; saccharide esters and ethers, such as sucrose stearate, sucrose cocoate and sorbitan stearate, and mixtures thereof, fatty acid esters (such as a C8-C24 and alternatively C16-C22 acid) of polyols, especially of glycerol or of sorbitol, such as glyceryl stearate, glyceryl stearate, glyceryl laurate, polyglyceryl-2 stearate, sorbitan tristearate or glyceryl ricinoleate.

Anionic surfactants include C16-C30 fatty acid salts, such as those derived from amines, for instance triethanolamine stearate; polyoxyethylenated fatty acid salts, such as those derived from amines or alkali metal salts, and combinations thereof; phosphoric esters and salts thereof, such as DEA oleth-10 phosphate or monocetyl monopotassium phosphate sulfosuccinates such as Disodium PEG-5 citrate lauryl sulfosuccinate and Disodium ricinoleamido MEA sulfosuccinate; alkyl ether sulfates, such as sodium lauryl ether sulfate; isethionates; acylglutamates such as disodium hydrogenated tallow glutamate, alkyl polyglucosides and combinations thereof.

The emulsion may further comprise an amphoteric surfactant, for instance N-acylamino acids such as N-alkylaminoacetates and disodium cocoamphodiacetate, and amine oxides such as stearamine oxide, or alternatively silicone surfactants, for instance dimethicone copolyol phosphates.

Dyestuffs

The emulsion may further comprise a dyestuff. The dyestuff may be selected from pulverulent dyestuffs (such as pigments and nacres) and water-soluble dyestuffs. For purposes of this application, the term "pigments" means white or colored, mineral or organic particles of any form, which are insoluble in the physiological medium, and which are intended to color the emulsion. For purposes of this application, the term "nacres" means iridescent particles of any form, produced especially by certain molluscs in their shell, or else synthesized.

The pigments may be white or colored, and mineral and/or organic. The mineral pigments include titanium dioxide, optionally surface-treated, zirconium oxide or cerium oxide, zinc oxide, iron oxide (black, yellow or red), chromium oxide, manganese violet, ultramarine blue, chromium hydrate, ferric blue, and metal powders, for instance aluminum powder or copper powder. The organic pigments include carbon black, pigments of D & C type, and lakes based on cochineal carmine or on barium, strontium, calcium or aluminum.

Mention may also be made of pigments with an effect, such as particles comprising a natural or synthetic, organic or mineral substrate, for example glass, acrylic resins, polyester, polyurethane, polyethylene terephthalate, ceramics or aluminas, said substrate being uncoated or coated with metallic substances, for instance aluminum, gold, silver, platinum, copper or bronze, or with metal oxides, for instance titanium dioxide, iron oxide or chromium oxide, and combinations thereof.

The nacres may be chosen from white nacreous pigments such as mica coated with titanium or with bismuth oxychloride, colored nacreous pigments such as titanium mica coated with iron oxides, titanium mica coated with ferric blue or with chromium oxide, titanium mica coated with an organic pigment of the abovementioned type, and also nacreous pigments based on bismuth oxychloride. Interference pigments, such as liquid-crystal or multilayer interference pigments, may alternatively be used.

Structuring Agents

The emulsion may further comprise a structuring agent. For purposes of this application, the term "structuring agent" means a compound capable of increasing the viscosity of the emulsion. The structuring agent makes it possible to obtain an emulsion that can have a texture ranging from fluid to solid textures.

The structuring agent may be present in the emulsion in an amount ranging from 0.1% to 20% by weight, alternatively ranging from 0.1% to 15% by weight and alternatively ranging from 0.5% to 10% by weight, relative to the total weight of the emulsion.

The structuring agent may be selected from thickeners (oily-medium thickeners; aqueous-medium thickeners), organogelling agents, waxes, pasty compounds and gums.

The aqueous-medium thickener may be chosen from: hydrophilic clays, hydrophilic fumed silica, water-soluble cellulose-based thickeners, guar gum, xanthan gum, carob gum, scleroglucan gum, gellan gum, rhamsan gum, karaya gum or carrageenan gum, alginates, maltodextrins, starch and its derivatives, and hyaluronic acid and its salts, the polyglyceryl (meth) acrylate polymers sold under the names Hispagel or Lubragel by Hispano Quimica or Guardian, polyvinylpyrrolidone, polyvinyl alcohol, crosslinked acrylamide polymers and copolymers, or alternatively the crosslinked methacryloyloxyethyltrimethylammonium chloride homopolymers, associative polymers and especially associative polyurethanes and sodium acrylate blends. Such thickeners are described especially in patent application EP-A-1 400 234.

The oily-medium thickener may be chosen from: organophilic clays; hydrophobic fumed silicas; alkyl guar gums (with a C1-C6 alkyl group), such as those described in EP-A-708 114; oil-gelling polymers, for instance triblock polymers or star polymers resulting from the polymerization or copolymerization of at least one monomer containing an ethylenic group.

Alternatively, the structuring agent can be a wax. For the purposes of this application, the term "wax" means a lipophilic compound that is solid at room temperature (25° C.), which undergoes a reversible solid/liquid change of state, and which has a melting point of greater than or equal to 30° C., which may be up to 120° C.

The waxes may be hydrocarbon-based waxes, fluoro waxes and/or silicone waxes, and may be of plant, mineral, animal and/or synthetic origin. In particular, the waxes may have a melting point of greater than 30° C.

Suitable waxes include beeswax, carnauba wax or candelilla wax, paraffin, microcrystalline waxes, ceresin or ozokerite; synthetic waxes, for instance polyethylene waxes or Fischer-Tropsch waxes, and silicone waxes, for instance alkyl, alkoxy dimethicones containing from 16 to 45 carbon atoms or silsesquioxane resin wax as described in patent application publication WO2005100444.

Alternatively, the emulsion may contain a pasty compound, which may be selected from lanolin and its derivatives; polymeric or non-polymeric silicone compounds; polymeric or non-polymeric fluoro compounds; vinyl polymers, such as olefin homopolymers, olefin copolymers, hydrogenated diene homopolymers, and linear or branched oligomers, homopolymers or copolymers of alkyl (meth) acrylates, such as those containing a C8-C30 alkyl group; oligomers, homopolymers, and copolymers of vinyl esters containing C8-C30 alkyl groups; oligomers, homopolymers and copolymers of vinyl ethers containing C8-C30 alkyl groups; liposoluble polyethers resulting from the polyetherification between one or more C2-C100 (alternatively C2-C50) diols, esters, and combinations thereof. The esters include esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid. The pasty compounds of plant origin include a mixture of soybean sterols and of oxyethylenated (5 OE) oxypropylenated (5 OP) pentaerythritol.

Active Ingredients

As used herein, a "personal care active" means any compound or combination of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Some representative examples of active ingredients include; drugs, vitamins, minerals; hormones; topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

Useful active ingredients for use in the emulsion include vitamins and their derivatives, including "pro-vitamins". Vitamins useful herein include, but are not limited to, Vitamin $A_1$, retinol, C2 to C18 esters of retinol, vitamin E, tocopherol, esters of vitamin E, and combinations thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the International Nomenclature Cosmetic Ingredient Name (INCI) names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

Alternatively, the active ingredient used in the emulsion can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole, clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of this application are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antpsoriasis agents such as clobetasol propionate; anesthetic agents such as lidocaine; antipruritic agents; antidermatitis agents; and agents generally considered barrier films.

Alternatively, the active ingredient in the emulsion can be a protein, such as an enzyme. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said proteases include, but are not limited to, trypsin, chymotrypsin, pepsin, pancreatin and other mammalian enzymes; papain, bromelain and other botanical enzymes; subtilisin, epidermin, nisin, naringinase (L-rhammnosidase) urokinase and other bacterial enzymes. Said lipases include, but are not limited to, triacyl-glycerol lipases, monoacyl-glycerol lipases, lipoprotein lipases, e.g., steapsin, erepsin, pepsin, other mammalian, botanical, bacterial lipases and purified ones. Natural papain is useful as said enzyme. Further, stimulating hormones, e.g., insulin, can be used together with these enzymes to boost the effectiveness of them.

Alternatively, the active ingredient may be a sunscreen agent. The sunscreen agent can be selected from any sunscreen agent known in the art to protect skin from the harmful effects of exposure to sunlight. The sunscreen agent may be selected from an organic compound, an inorganic compound, or a combination thereof that absorbs ultraviolet (UV) light. Representative, non-limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer. These sunscreen agents can be selected as one or a combination of two or more.

Alternatively, the active ingredient may a plant extract. Alternatively, the active ingredient may be a self tanning agent such as but not limited to dihydroxyacetone and erythrulose or an insect repellent such as but not limited to ethyl butylacetylaminopropionate or plant extract such as citronella. The amount of active ingredient present in the emulsion will vary depending on factors including the type of active ingredient selected and the method of use of the emulsion, however, the amount of active ingredient may range from 0.05 wt % to 50 wt %, alternatively 1 wt % to 25 wt %, or alternatively 1 to 10 wt %, based on the weight of the emulsion.

Alternatively, the active ingredient may be an antiperspirant and/or deodorant agent. Some examples of antiperspirant agents and deodorant agents are Aluminum Chloride, Aluminum Zirconium Tetrachlorohydrex GLY, Aluminum Zirconium Tetrachiorohydrex PEG, Aluminum Chlorohydrex, Aluminum Zirconium Tetrachiorohydrex PG, Aluminum Chlorohydrex PEG, Aluminum Zirconium Trichlorohydrate, Aluminum Chiorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

Fragrance

Fragrance or perfume can also be added to the emulsion. The fragrance can be any perfume or fragrance ingredient commonly used in the perfume industry. These fragrance ingredients may belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these fragrance ingredients are described in detail in standard textbook references such as Perfume and Flavour Chemicals, 1969, S. Arctander, Montclair, N.J.

Preservatives

When making an emulsion with the emulsifiers described herein, it may be desirable to add various preservatives such as the parabens, BHT, BHA, phenoxy ethanol, as listed on the Annex VI, Part 1 of the European Cosmetic directive—LIST OF PRESERVATIVES WHICH COSMETIC PRODUCTS MAY CONTAIN. When present, the amount of preservative may range from 0.01% to 5% by weight based on the weight of the emulsion.

The emulsion is suitable for use in personal care products. Such personal care products are exemplified by antiperspirants and deodorants, skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, wrinkle fillers, skin imperfection hiders, skin surface smoothers, eyelash curlers, nail varnishes, hair make-up products, eye shadows, body makeups, and powders, medicament creams, pastes or sprays including anti-acne, dental hygienic, antibiotic, healing promotive, nutritive and the like, which may be preventative and/or therapeutic.

EXAMPLES

The following examples are included to demonstrate the invention to one of ordinary skill. However, those of ordinary skill in the art should, in light of the present disclosure, appreciate that many changes can be made in the specific embodiments which are disclosed and still obtain a like or similar result without departing from the spirit and scope of the invention. All amounts, ratios, and percentages are by weight unless otherwise indicated.

Example 1

Copolymer Preparation

A 1000 ml flask equipped with Dean-Stark trap, reflux condenser, temperature controller and heating mantle, and a stirrer was charged with 295.6 g DOW CORNING® 4-2737 silanol terminated polydimethylsiloxane, 44.7 g of DOW CORNING® 5 cSt 200 Fluid, 233.2 g octadecylmethyldimethoxysilane from Gelest, Inc., and 11.5 g of aminopropylmethyldiethoxysilane from Sigma Aldrich. This combination of ingredients was heated at 80° C., 0.9 g of KOH was added to the resulting mixture, and a nitrogen purge was started through the reactor. After two hours, 7 g water was added with stirring for two more hours. When condensation in the Dean-Stark trap stopped, an additional 7 g water was added, and the mixture was heated to 120° C. After 2 hours, the nitrogen flow was stopped, and the mixture was heated to 150° C. with stirring. After 4 hours, the mixture was cooled to 70° C. and 0.96 g of glacial acetic acid was added. In the next step, vacuum was applied to remove volatiles at 150° C. for 4 hours. The resulting mixture was cooled to 70° C. and filtered through 0.45 micron pore size filter to form an alkyl modified aminosiloxane.

A 1000 ml flask was charged with 200 g of the above alkyl amino siloxane, and 3.66 g of delta-gluconolactone and 203.66 g of isopropanol were added. The mixture was heated for four hours at 74° C. After four hours, the isopropanol was then removed by vacuum stripping at 74° C.

Example 2

Copolymer Synthesis

Example 1 is repeated, except that oil is added after the alkyl amino siloxane, delta-gluconolactone, isopropanol are combined and heated for four hours at 74° C. After the oil is added, the isopropanol is then removed by vacuum stripping at 74° C. The oil used is 5 cSt 200 Fluid in an amount sufficient to make a combination of 25% copolymer from example 1 and 75% oil.

Examples 3 and 4

Copolymer Synthesis

Examples 1 and 2 are repeated, except that synthesis is performed with less than a stochiometric amount of delta-gluconolactone in the second step, so the second step is modified as follows.

A 1000 ml flask is charged with 200 g of the above alkyl amino siloxane, 1.83 g of delta-gluconolactone, and 201.83 g of isopropanol. The mixture is heated for four hours at 74° C. After four hours, there is option to add oil. The alcohol is removed by vacuum stripping at 74° C. in full vacuum. For example 3, no oil is added before vacuum stripping to remove isopropanol. For example 4, the oil used is 5 cSt 200 Fluid in an amount sufficient to make a combination of 25% copolymer from example 1 and 75% oil

Examples 5 and 6

Copolymer Synthesis, Capping

The copolymers prepared in examples 3 and 4 are subjected to a capping step. Capping is performed by charging 1000 ml flasks, each with 200 g of a copolymer of example 3 or a copolymer/oil combination of example 4 above. The following ingredients are added to each flask: 2.78 g of dodecyl/tetradecyl glycidyl ether, and 202.78 g of isopropanol. The mixtures are heated for 8 hours at 74° C., and the isopropanol is then removed by vacuum stripping at 74° C. with full vacuum.

Examples 7 and 8

Compatibility

Two copolymers were prepared by repeating the method of example 1. Each copolymer had formula:

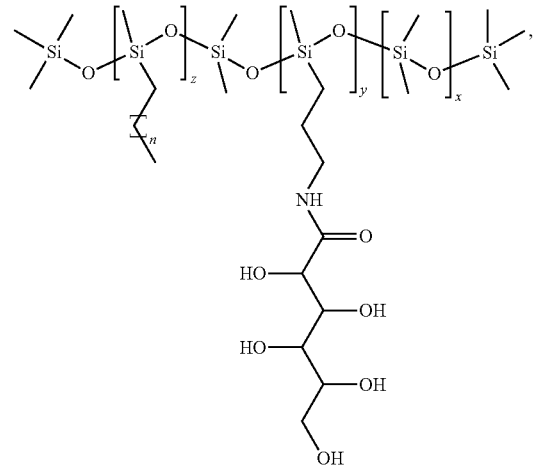

where subscript y was 0.75, subscript x was 65, subscript z was 10 and subscript n was 16.

Comparative Example 9

Compatibility

A comparative saccharide siloxane was prepared in a 500 ml flask that was equipped with stirrer, reflux condenser, and temperature controller by combining 100 g of trimethylsiloxy terminated poly(dimethyl/methyl(aminoethylaminoisobutyl) siloxane), with a DP of 44 and an average 2.57 of aminoethylaminoisobutyl functional groups per molecule and 6.61 g of delta-gluconolactone. Then 106.6 g of ethanol was added, and the mixture was reacted at 74° C. After four hours of reaction, 40.12 g of dodecyl/tetradecyl glycidyl ether was added and reacted for 8 hours. At the completion of the reaction ethanol was removed by stripping at 74° C. at full vacuum.

The reaction scheme of the second step was as follows.

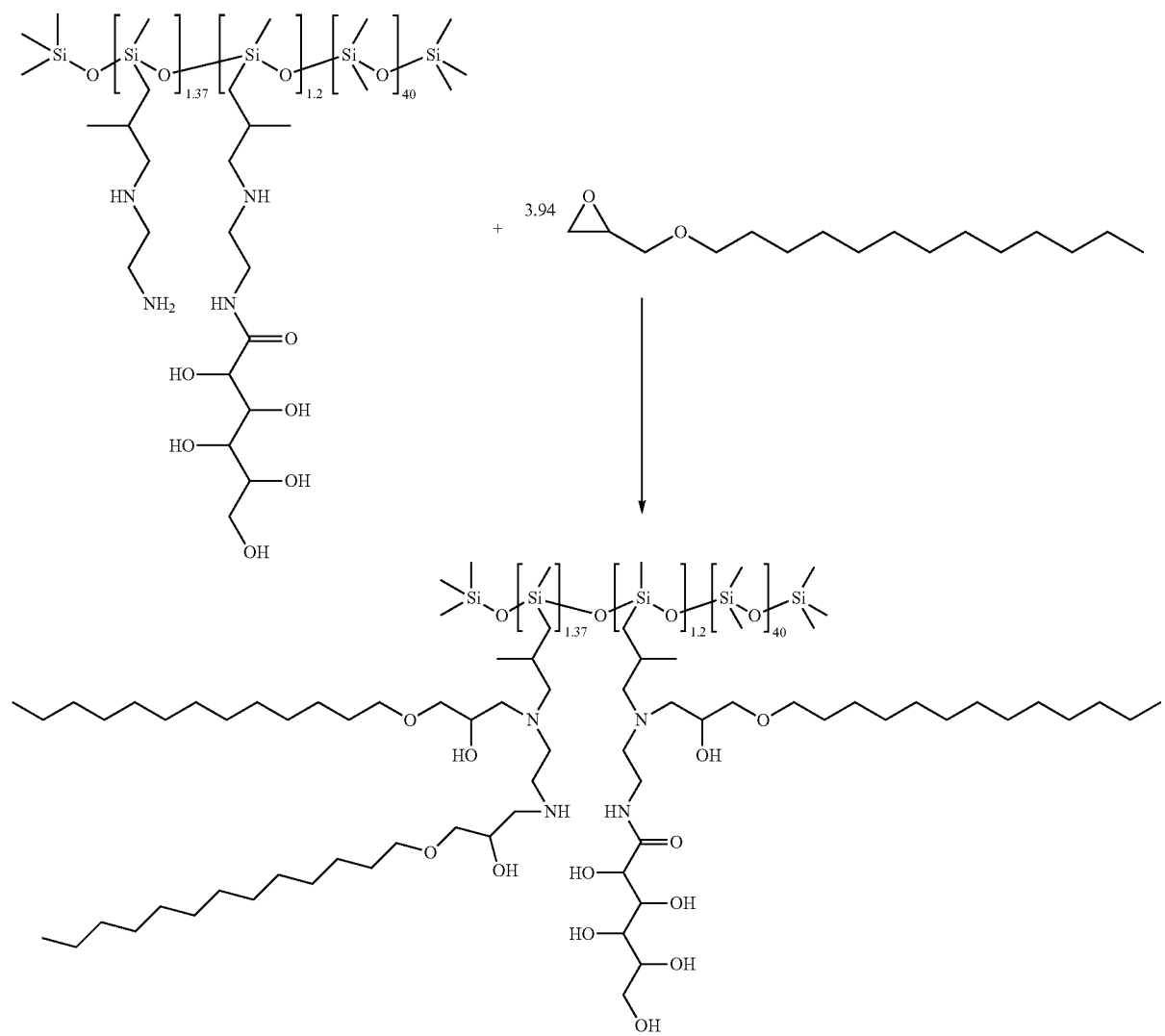

H-NMR was used to confirm the structure in the reaction scheme above.

Comparative Example 10

Compatibility

For comparative purposes, a commercially available emulsifier, ABIL® EM 90 a cetyl polyethylene glycol, polypropylene glycol functional polydimethylsiloxane from Evonik Goldschmidt Corporation of Hopewell, Va., U.S.A. was used.

In examples 7 and 8, and comparative examples 9 and 10, the copolymers were dispersed in various oils to determine compatibility. In each sample, 9 grams of oil and 1 g of copolymer were mixed under ambient conditions. The results are in Table 1.

TABLE 1

Compatibility Test Results

| | Example | | | |
|---|---|---|---|---|
| | Example 7 | Example 8 | Comparative Example 9 | Comparative Example 10 |
| | Emulsifier | | | |
| Oil | Co-polymer of example 7 | Copolymer of example 8 | Comparative saccharide siloxane of example 9 | Abil 90 EM |
| 5 cSt 200 Fluid | clear | clear | slightly hazy | hazy |
| FZ-3196 | clear | clear | clear | clear |
| Isohexadecane | clear | clear | clear | clear |
| Isopropyl Myristate | clear | clear | clear | clear |
| Alkyl Benzoate | clear | clear | slightly hazy | clear |
| Capric Triglyceride | clear | hazy | hazy | clear |
| Mineral Oil | clear | hazy | hazy | clear |

In Table 1, 5 cSt 200 Fluid refers to a polydimethylsiloxane having viscosity of 5 cSt available from Dow Corning Corporation as DOW CORNING® 200 Fluid, and FZ-3196 refers to a polydialkylsiloxane fluid available from Dow Corning Corporation.

Emulsion Examples 11 to 18

Process for Making an Emulsion with Stirrer Mixer

Emulsions containing the ingredients in Table 2 using a copolymer as emulsifier were prepared by the following method.
1. The ingredients of phase A were mixed together to obtain a homogeneous mix.
2. The ingredients of phase B were mixed together to obtain a homogeneous mix
3. Phase B was added to phase A under mixing (with a cross stirrer). While adding phase B, mixing speed increased from 700 rpm to 1000 rpm.
4. After all phase B was added, the resulting product was mixed for 1 minute at 1000 rpm and 5 minutes at 2000 rpm. A coarse emulsion was obtained.
5. A 100 gram sample of the coarse emulsion was passed through a high shear mixing apparatus for 15 seconds to reduce the particle size. The high shear mixing apparatus was a lab mixer from Silverson Machines Ltd. of England. A fine emulsion was obtained.

The copolymer from example 1 had formula:

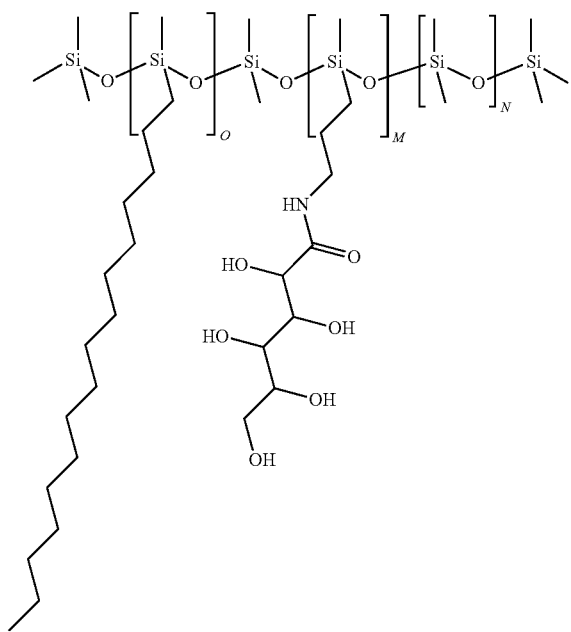

where subscript M was 0.75, subscript N was 65, and subscript O was 10.

Process for Making an Emulsion with Dental Mixer

Emulsions could be prepared using a copolymer as emulsifier by the following method.
1. The ingredients of phase A were mixed together.
2. The ingredients of phase B were mixed together.
3. Phase B was added to phase A in 5 g increments.
4. After addition of each increment, the resulting product was mixed for 40 seconds at 3400 rpm in a dental mixer (DAC 150 Series—SpeedMixer™).
5. Steps 3 and 4 were repeated until all phase B was added to obtain a final emulsion.

Reference Example

Emulsion Stability

Stability of the emulsions 11 to 18 prepared herein was evaluated during storage of samples of each emulsion for 6 months at room temperature (RT), 40° C., and 50° C. Stability was measured by visual inspection. The results are in Table 2 below.

Reference Example

Freeze/Thaw Stability of Emulsions

Samples of the emulsions 11 to 18 prepared herein were evaluated for freeze/thaw stability. The procedure was as follows:
1. Emulsion samples were refrigerated at 4° C. for a minimum of 12 hours and then stored at RT for few hours.
2. Emulsion stability was evaluated. Stability was measured by visual inspection.
3. Steps 1 and 2 were repeated five times. The results are in Table 3 below.

TABLE 2

| | Ingredient | Emulsion Sample | | | | | | | |
|---|---|---|---|---|---|---|---|---|---|
| | | 11 | 12 | 13 | 14 | 15 | 16 | 17 | 18 |
| | | Amount by weight | | | | | | | |
| | | % | % | % | % | % | % | % | % |
| Phase A | Copolymer | 1 | 2 | 2 | 1 | 2 | 1 | 2 | 1 |
| | Xiameter® PMX-200 Silicone Fluid 5CS | / | / | 16 | / | | | / | / |
| | Xiameter® PMX-Silicone 200 Fluid 5CS/Crodamol GTCC (50%/50%) | 18 | 16 | / | / | / | 18 | 16 | 9 |
| Phase B | Mineral Oil | | | | 18 | 16 | / | / | |
| | Water | 74 | 74 | 74 | 74 | 74 | 54 | 84 | 84 |
| | Glycerin | 5 | 5 | 5 | 5 | 5 | 5 | 5 | 5 |
| | NaCl | 1 | 1 | 1 | 1 | 1 | 1 | 1 | 1 |

In the tables, Crodamol GTCC refers to a medium chain triglyceride of low viscosity, which is used as an emollient. Crodamol GTCC is commercially available from Croda, Inc. of Edison, New Jersey, U.S.A.

TABLE 3

| Results | | | | | | | | |
|---|---|---|---|---|---|---|---|---|
| Viscosity (Brookfield DV-II-Spindle 6, 2.5 rpm) | | | | | | | | |
| 1 day | / | 126000 | 44000 | Broken after High shear mixing | 15600 | 1600 | 1000 | Broken after High shear mixing |
| 1 week | / | 156000 | 42800 | / | 10400 | 1600 | 950 | / |
| 2 weeks | / | 157000 | 38400 | / | 10800 | 2000 | 800 | / |

TABLE 3-continued

| | | | Results | | | | | |
|---|---|---|---|---|---|---|---|---|
| 3 weeks | / | 170000 | 38000 | / | 12300 | 1600 | 800 | / |
| 1 month | / | 167000 | 34200 | / | 14400 | 1600 | / | / |
| 2 months | / | 166000 | 36800 | / | / | / | / | / |
| 3 months | / | 174000 | 32800 | / | / | / | / | / |
| 4 months | / | 175000 | 34800 | / | / | / | / | / |
| | | | Stability | | | | | |
| At RT | Stable at least 4 months | Stable at least 4 months | Stable at least 4 months | / | Stable for 2 months | Stable at least of 1 month | Stable at least of 1 month | / |
| At 40 C. | Stable for 3 months | Stable at least 4 months | Stable at least 4 months | / | Stable for 3 weeks | Stable for 2 weeks | Stable for 3 weeks | / |
| At 50 C. | Stable for 2 months | Stable at least 4 months | Stable at least 4 months | / | Stable for 3 weeks | Stable for 2 weeks | Stable for 2 weeks | / |
| F/T Cycle | 0 | 0 | 0 | / | 0 | 4 | At least 3 cycles | / |
| Emulsion Sample | 11 | 12 | 13 | 14 | 15 | 16 | 17 | 18 |

INDUSTRIAL APPLICABILITY

The copolymer described above is useful as an emulsifier for water in oil (w/o) type emulsions, particularly where the oil comprises a silicone. Alternatively, the copolymer described above is useful as an emulsifier for w/o type emulsions where the oil comprises an organic oil. The copolymer may provide an emulsion with low odor, i.e., lower odor than as compared to emulsions containing silicone polyether emulsifiers. The copolymer may also provide an emulsion which is nonirritating to the skin, i.e., the a personal care product containing a safe and effective amount of the emulsion containing the copolymer is suitable for application to skin.

The invention claimed is:

1. A saccharide siloxane copolymer of formula:

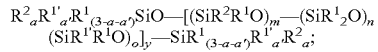

where
each $R^1$ can be the same or different and each $R^1$ comprises hydrogen, an alkyl group of 1 to 12 carbon atoms, an organic group, or a group of formula $R^3$-Q;
Q comprises an epoxy, cycloalkylepoxy, primary or secondary amino, ethylenediamine, carboxy, halogen, vinyl, allyl, anhydride, or mercapto functionality;
each $R^{1'}$ is a monovalent organic group with an average of at least 16 carbon atoms;
subscript m has an average value ranging from 0 to 10,000;
subscript n has an average value ranging from 0 to 10,000;
subscripts m, n, and o may be the same or different;
subscript o has an average value ranging from 0 to 10,000;
each subscript a is independently 0, 1, 2, or 3;
each subscript a' is independently 0, 1, 2, or 3;
subscript y is an integer such that the copolymer has a molecular weight less than 1 million, and subscript y has a value of at least 1; provided when each subscript a' is 0, then subscript o is greater than 0;
each $R^2$ has formula $Z$-$(G^1)_b$-$(G^2)_c$, and there is an average of at least one $R^2$ per copolymer molecule, where $G^1$ is a saccharide component comprising 5 to 12 carbon atoms,
a quantity (b+c) has a value ranging from 1 to 10, and subscript b or subscript c can be 0,
$G^2$ is a saccharide component comprising 5 to 12 carbon atoms additionally substituted with organic or organosilicon radicals, each Z is a linking group and is independently selected from the group consisting of:

—$R^3$—NHC(O)—$R^4$—;
—$R^3$—NHC(O)O—$R^4$—;
—$R^3$—NH—C(O)—NH—$R^4$—;
—$R^3$—C(O)—O—$R^4$—;
—$R^3$—O—$R^4$—;
—$R^3$—CH(OH)—$CH_2$—O—$R^4$—;
—$R^3$—S—$R^4$—;
—$R^3$—CH(OH)—$CH_2$—NH—$R^4$—;
—$R^3$—N($R^1$)—$R^4$—;
—NHC(O)—$R^4$—;
—NHC(O)O—$R^4$—;
—NH—C(O)—NH—$R^4$—;
—C(O)—O—$R^4$—;
—O—$R^4$—;
—CH(OH)—$CH_2$—O—$R^4$—;
—S—$R^4$—;
—CH(OH)—$CH_2$—NH—$R^4$—;
—N($R^1$)—$R^4$—;
—$R^3$—NHC(O)—;
—$R^3$—NHC(O)O—;
—$R^3$—NH—C(O)—NH—;
—$R^3$—C(O)—O—;
—$R^3$—O—;
—$R^3$—CH(OH)—$CH_2$—O—;
—$R^3$—S—;
—$R^3$—CH(OH)—$CH_2$—NH—;
—$R^3$—N($R^1$)—;
—$R^3$—N($R^8$)—C(O)—$R^4$—,
—$R^3$—CH(OH)—$CH_2$—N($R^8$)—$R^4$—, or
—$R^3$—CH(N($R^4$)($R^8$))$CH_2$OH;

where each $R^3$ and each $R^4$ are divalent spacer groups comprising a group of formula $(R^5)_r(R^6)_s(R^7)_t$,
where at least one of subscripts r, s and t is 1, and each $R^5$ and each $R^7$ independently an alkylene group of 1 to 12 carbon atoms;
each $R^6$ is —N($R^8$)—, where $R^8$ is selected from $R^3$, a group of formula Z—X, a monovalent hydrocarbon group, or a reaction product of —N(H)— with an epoxy functional group, a cycloalkylepoxy functional group, a glycidyl ether functional group, an acidic anhydride functional group, or a lactone;
each X is independently a divalent carboxylic acid, phosphate, sulfate, sulfonate or quaternary ammonium radical, and
with the provisos that
at least one of $R^3$ and $R^4$ must be present in the linking group, and
each $R^3$ and each $R^4$ may be the same or different.

2. The copolymer of claim 1, where each Z is independently selected from the group consisting of: $-R^3-N(R^8)-C(O)-R^4-$, $-R^3-CH(OH)-CH_2-N(R^8)-R^4-$, or $-R^3-CH(N(R^4)(R^8))CH_2OH$.

3. The copolymer of claim 1, where subscripts m and n are integers from 0 to 500 and may be the same or different.

4. The copolymer of claim 1, where subscript o is an integer from 0 to 2,500.

5. The copolymer of claim 1 wherein R1' is an alkyl group with an average of at least 16 carbon atoms.

6. The copolymer of claim 5 wherein R1' is an alkyl group with an average of from 16 to 40 carbon atoms.

7. The compolymer of claim 1 wherein each Z is a linking group and is independently selected from the group consisting of:
$-R^3-NHC(O)-R^4-$;
$-R^3-NHC(O)O-R^4-$;
$-R^3-NH-C(O)-NH-R^4-$;
$-R^3-C(O)-O-R^4-$;
$-R^3-CH(OH)-CH_2-O-R^4-$;
$-R^3-S-R^4-$;
$-R^3-CH(OH)-CH_2-NH-R^4-$;
$-R^3-N(R^1)-R^4-$;
$-NHC(O)-R^4-$;
$-NHC(O)O-R^4-$;
$-NH-C(O)-NH-R^4-$;
$-C(O)-O-R^4-$;
$-CH(OH)-CH_2-O-R^4-$;
$-S-R^4-$;
$-CH(OH)-CH_2-NH-R^4-$;
$-N(R^1)-R^4-$;
$-R^3-NHC(O)-$;
$-R^3-NHC(O)O-$;
$-R^3-NH-C(O)-NH-$;
$-R^3-C(O)-O-$;
$-R^3-O-$;
$-R^3-CH(OH)-CH_2-O-$;
$-R^3-S-$;
$-R^3-CH(OH)-CH_2-NH-$;
$-R^3-N(R^1)-$;
$-R^3-N(R^8)-C(O)-R^4-$,
$-R^3-CH(OH)-CH_2-N(R^8)-R^4-$, or
$-R^3-CH(N(R^4)(R^8))CH_2OH$.

8. A method for making a saccharide siloxane copolymer according to claim 1, where the method comprises the steps of:
i) reacting an organofunctional polyorganosiloxane with a sugar moiety to produce the saccharide siloxane copolymer in the presence of a solvent;
optionally ii) removing a portion of the solvent; and
optionally iii) adding an oil.

9. The method of claim 8, where the oil is added before and/or during step i).

10. The method of claim 8 where the oil is added during and/or after step ii).

11. The method of claim 8, further comprising iv) removing the solvent.

12. The method of claim 8, where step i) is performed by reacting ingredients comprising:
(A) an amino-functional polyorganosiloxane, and
(B) a sugar lactone.

13. The method of claim 8, where step i) is performed by reacting ingredients comprising:
(A) an epoxy-functional polyorganosiloxane, and
(B) an n-alkyl glucamine.

14. The method of claim 8, where step i) is performed by a method comprising:
1) reacting (a) an n-alkyl-glucamine with (b) an alkenyl functional epoxy compound, and
2) hydrosilylating the product of step 1) with (c) a polyorganohydrogensiloxane.

15. The method of claim 14, where the product of step i) contains secondary amine functionality, further comprising a step of reacting the product of step i) with a capping agent selected from a lactone, a halogenated unsaturated compound, an epoxy functional compound, or an acid anhydride.

16. The method of claim 8, where the solvent is present, and the solvent is an alcohol selected from methanol, ethanol, n-propanol, isopropanol, 2-propanol, isobutanol, n-butanol, and combinations thereof.

17. The method of claim 8, where the oil is present, and the oil is a silicone oil.

18. The method of claim 17, where the oil is a polydialkylsiloxane.

19. The method of claim 8, where the oil is present, and the oil is an organic oil selected from a hydrocarbon oil, an ester, a vegetable oil, a mineral oil, or a fatty alcohol.

20. The method of claim 8, where the copolymer and the oil are present in an amounts such that a weight ratio of copolymer/oil ranges from 1/1 to 1/50.

21. A method for making a copolymer according to claim 1, comprising:
1) equilibration and/or condensation reaction of
i) a short chain silanol functional polyorganosiloxane,
ii) an aminodialkoxyalkylsilane,
iii) a dialkyldialkoxysilane, where at least one of the alkyl groups on the dialkyldialkoxysilane is $R^{1'}$, and
iv) an endblocker; and
2) reaction of the product of step 1) with a sugar lactone.

22. The method of claim 21, where the sugar lactone is an aldonolactone.

23. The method of claim 21, further comprising step 3) reacting the product of step 2) with a capping agent selected from a lactone, a halogenated unsaturated compound, an epoxy functional compound, or an acid anhydride.

24. The method of claim 23, where the lactone in step 3) is selected from: butyrolactone, epsilon caprolactone, gamma gluconolactone, delta gluconolactone, and lactobionolactone.

25. The method according to claim 23, where the halogenated unsaturated compound is an alkenyl chloride.

26. The method according to claim 23, where the epoxy functional compound is selected from allyl epoxy functional compounds, cycloalkylepoxy functional compounds, glycidyl ether functional compounds, and glycidol.

27. The method according to claim 23, where the acid anhydride comprises acetic anhydride, chloroacetic anhydride, propionic anhydride, crotonic anhydride, methacrylic anhydride, butyric anhydride, isobutyric anhydride, diethyl pyrocarbonate, or 4-pentenoic anhydride.

28. A composition comprising:
(A) the copolymer according to claim 1, and
(B) an additional ingredient.

29. The composition of claim 28, where ingredient (B) comprises:
(ii) a carrier medium suitable to permit topical application composition to a portion of the body,
(iii) a cross-linker,
(iv) a surfactant, or
(v) a combination thereof.

30. The composition of claim 29, where ingredient (iii) is present, and ingredient (iii) comprises water.

31. The composition of claim 30, where the composition is an emulsion.

32. A composition according to claim 28, where the composition is a personal care composition adapted to provide a benefit to the portion of the body to which it is applied.

33. An emulsion comprising:
A) a discontinuous aqueous phase,
B) a continuous oil phase, and
C) an emulsifier, where the emulsifier comprises a copolymer according to claim 1.

34. A method of making the emulsion of claim 33, comprising:
1) dispersing the emulsifier in the oil phase,
2) adding the aqueous phase to the oil phase, and
optionally 3) subjecting the product of step 2) to shear.

35. A composition comprising:
I) the emulsion of claim 33, and
II) an additive.

36. The composition of claim 35, where ingredient II) is selected from: silicones, aerosols, anti-oxidants, cleansing agents, colorants, conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, antiperspirants, anti-dandruff, anti-acne, anti-carie and wound healing-promotion agents, an additional oil, a hydrophilic medium, a filler, a fiber, a film forming polymer, an emulsifier, a dyestuff, a structuring agent, an active ingredient, a fragrance, a preservative, and combinations thereof.

37. A composition according to claim 36, where the composition is a personal care composition adapted to provide a benefit to a portion of the body to which it is applied.

38. The composition of claim 37, where the personal care composition is selected from antiperspirants, deodorants, skin creams, skin care lotions, moisturizers, acne-remover facial treatments, wrinkle-remover facial treatments, personal and facial cleansers, bath oils, perfumes, colognes, sachets, sunscreens, pre-shave and after-shave lotions, shaving soaps, shaving lathers, hair shampoos, hair conditioners, hair colorants, hair relaxants, hair sprays, mousses, gels, permanents, depilatories, cuticle coats, make-ups, color cosmetics, foundations, concealers, blushes, lipsticks, eyeliners, mascara, oil removers, color cosmetic removers, wrinkle fillers, skin imperfection hiders, skin surface smoothers, eyelash curlers, nail varnishes, hair make-up products, eye shadows, body makeups, powders, medicament creams, anti-acne pastes or sprays, dental hygienic pastes or sprays, antibiotic pastes or sprays, healing promotive pastes or sprays, and nutritive pastes or sprays.

* * * * *